(12) United States Patent
Przekwas et al.

(10) Patent No.: US 11,145,418 B2
(45) Date of Patent: Oct. 12, 2021

(54) SYSTEM AND METHOD FOR MODEL-BASED CALCULATION OF BLAST EXPOSURE

(71) Applicants: CFD Research Corporation, Huntsville, AL (US); The Government of The United States, as represented by The Secretary of The Army, Fort Detrick, MD (US)

(72) Inventors: Andrzej Przekwas, Huntsville, AL (US); Harsha T. Garimella, Huntsville, AL (US); Timothy Zehnbauer, Huntsville, AL (US); Zhijian Chen, Huntsville, AL (US); Vincent Harrand, Huntsville, AL (US); Raj Kumar Gupta, Fort Detrick, MD (US); Gary Kamimori, Laurel, MD (US); Walter Carr, Bethesda, MD (US)

(73) Assignees: CFD RESEARCH CORPORATION, Huntsville, AL (US); The Government of The United States, as represented by the Secretary of the Army, Fort Detrick, MD (US)

(*) Notice: Subject to any disclaimer, the term of this patent is extended or adjusted under 35 U.S.C. 154(b) by 141 days.

(21) Appl. No.: 16/697,038

(22) Filed: Nov. 26, 2019

(65) Prior Publication Data
US 2020/0303081 A1    Sep. 24, 2020

Related U.S. Application Data

(63) Continuation-in-part of application No. 16/356,997, filed on Mar. 18, 2019, now Pat. No. 10,983,020.

(51) Int. Cl.
*G16H 50/50* (2018.01)
*G01L 5/00* (2006.01)
(Continued)

(52) U.S. Cl.
CPC ........... *G16H 50/50* (2018.01); *A61B 5/4561* (2013.01); *A61B 2503/12* (2013.01)

(58) Field of Classification Search
CPC ..... G01L 5/00; G01L 5/0052; G01L 5/14–18; G01N 3/313; G16H 50/50; A61B 5/5461; A61B 2503/12; F42B 23/24
See application file for complete search history.

(56) References Cited

U.S. PATENT DOCUMENTS

| | | | | |
|---|---|---|---|---|
| 7,597,047 | B2 * | 10/2009 | Doyle | ..................... F41A 33/04 |
| | | | | 102/355 |
| 7,660,692 | B2 * | 2/2010 | Van Albert | .............. F41J 5/056 |
| | | | | 702/127 |

(Continued)

*Primary Examiner* — Nguyen Q. Ha
(74) *Attorney, Agent, or Firm* — Maschoff Brennan; Jonathan M. Benns

(57) ABSTRACT

A method of calculating blast injury metrics in a weapon training/IED blast scene can include: reconstructing topological layout of the scene having at least one real subject and a blast source; obtaining anthropometric and posture data for each real subject; obtaining anatomical soldier model for each real subject; identifying real position of at least one real pressure sensor on each soldier during a blast; positioning a virtual sensor on each anatomical soldier model to correspond with real pressure sensor on the real subject; calculating weapon signature of the blast source, the weapon signature including pressure versus time for a blast from the blast source; generating simulated pressure traces on each anatomical soldier model at east virtual pressure sensor; calculating blast injury metrics for the at least one real subject; and generating a report that includes the blast injury metrics for the at least one real subject.

20 Claims, 29 Drawing Sheets

(51) Int. Cl.
   *G01L 5/14*   (2006.01)
   *A61B 5/00*   (2006.01)

(56) References Cited

U.S. PATENT DOCUMENTS

| | | | |
|---|---|---|---|
| 8,400,636 B2* | 3/2013 | Smith | G01P 15/06 |
| | | | 356/402 |
| 2011/0246402 A1* | 10/2011 | Burman | G08B 13/1672 |
| | | | 706/14 |
| 2016/0317383 A1* | 11/2016 | Stanfield | A61B 5/6804 |
| 2017/0019639 A1* | 1/2017 | Bae | H04N 7/18 |

* cited by examiner

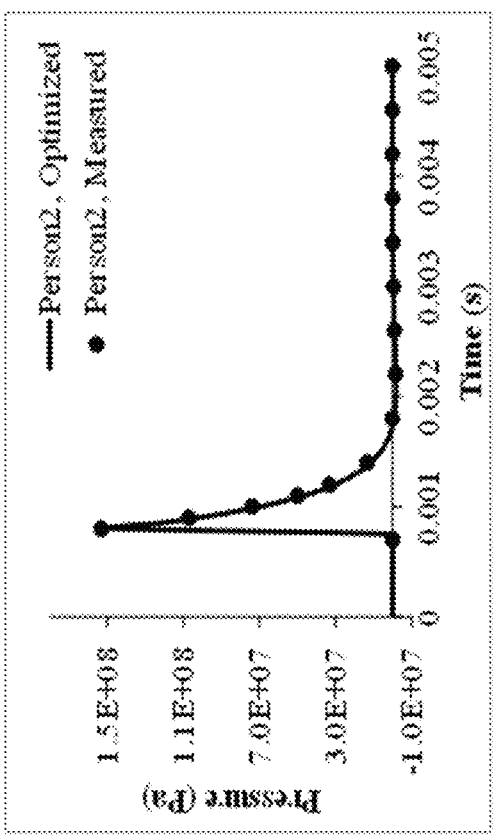
Fig.16A
Fig.16B
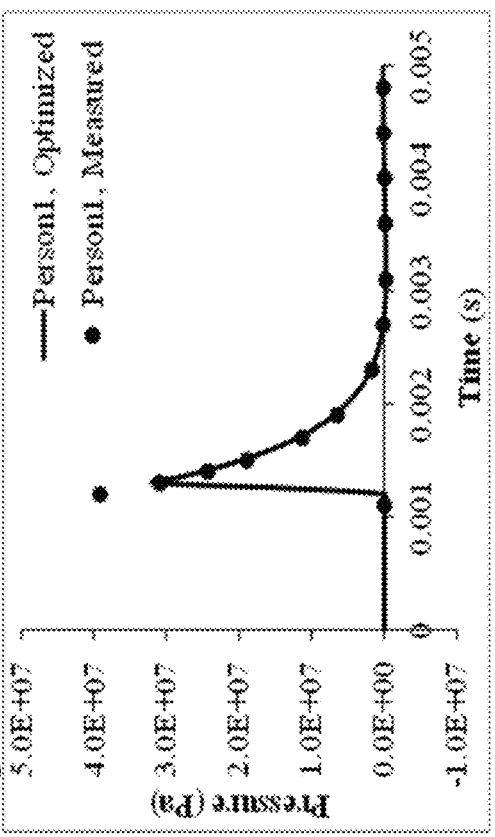
Fig.16C
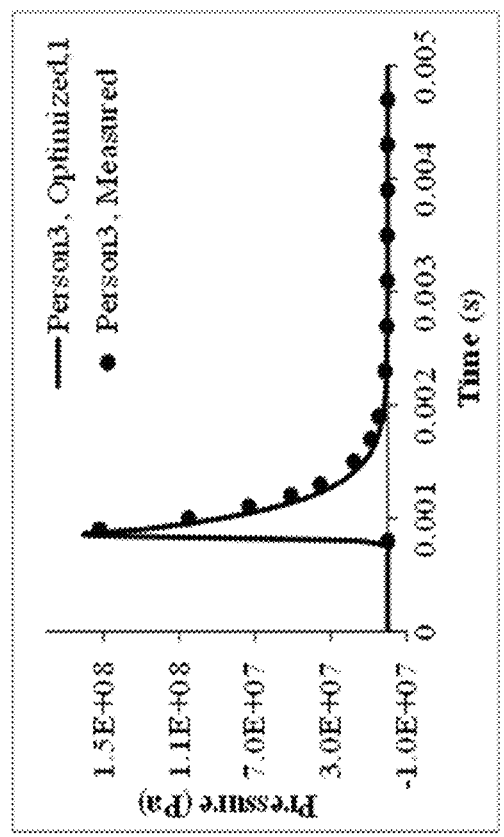
Fig.16D

SYSTEM AND METHOD FOR MODEL-BASED CALCULATION OF BLAST EXPOSURE

CROSS-REFERENCE TO RELATED APPLICATIONS

This application is a continuation-in-part of U.S. patent application Ser. No. 16/356,997 filed Mar. 18, 2019, which application is incorporated herein by specific reference in its entirety.

GOVERNMENT RIGHTS

This invention was made with government support under W81XWH-17-C-0216 awarded by the U.S. Army Medical Research and Materiel Command. The government has certain rights in the invention.

BACKGROUND

Improvised explosive devices (IED) have become the common weapon used against military targets and in terrorism acts against civilian populations. Such devices can be deployed as roadside bombs, vehicle mounted explosives, suicide vests and other forms, causing serious damage including loss of life [Homeland Department, 2018, Feldhoff, et. al., 1999]. The monitor report [Overton et. al., 2017] shows there were 7223 IED explosive incidents worldwide from year 2011 to 2016, which caused a total of 133,317 deaths and injuries (e.g., equal to 22,219 per year). Among all deaths and injuries civilian's deaths and injuries are 109,696 and armed actor's deaths and injuries are 23,621. The civilian casualty rate is 81% during this period. The blast from the IED can have serious health consequences.

Additionally, military and law enforcement personnel can use high power rifles and explosive materials during training and in combat, and thereby are often exposed to blast waves. Training of breachers involves explosive materials generating blast waves, while training of gunners, snipers, artillery and mortar crews are exposed to blast waves generated by high power weapons, such as the mortar, artillery and recoilless rifles. Repeated exposure to blast waves, even to low-level blasts, during military training may cause neurocognitive effects [Carr et al 2015, 2016; Kamimori et al 2017].

The U.S. Department of Defense (DoD) has been taking steps to mitigate any potentially harmful effects from blast exposure. The DoD has developed wearable blast gauges that can be used to measure the overpressure levels on service members exposed to blast waves of any type, from any source, at any blast level. However, the data collected from these pressure gauges do not allow accurate determination of blast loads on the human body and specific organs, such as the head, torso, ears, and eyes. Moreover, current blast gauges may have limited accuracy at lower blast pressures.

Therefore, it would be advantageous to have improved model-based calculations of blast exposure on humans during military training and combat. It would also be helpful to be able to record the data and calculation results for use in tracking purposes and for minimizing adverse effects of blast loading on humans.

SUMMARY

In some embodiments, a method of calculating blast injury metrics in a scene can include: reconstructing topological layout of the scene having at least one real subject and a blast source; obtaining anthropometric and posture data for each real subject; obtaining anatomical soldier model for each real subject; identifying real position of at least one real pressure sensor on each soldier during a blast; positioning a virtual sensor on each anatomical soldier model to correspond with real pressure sensor on the real subject; calculating weapon signature of the blast source, the weapon signature including pressure versus time for a blast from the blast source; generating simulated pressure traces on each anatomical soldier model at each virtual pressure sensor; calculating blast injury metrics for the at least one real subject; and generating a report that includes the blast injury metrics for the at least one real subject. In some aspect, the blast injury metrics include at least one of peak overpressure, positive impulse, negative impulse, organ specific injury criteria, and injury diagnosis, or the like. In some aspects, the scene includes position and orientation of the at least one real subject and blast source relative to each other. In some aspects, the method can include identifying a relative position for each real subject with respect to each other by using the blast source position and orientation as a reference. In some aspects, the method can include generating the anatomical soldier model for each real subject. In some aspects, the anatomical soldier model includes a three dimensional skin model equipped with clothing and protective armor articulated into a pose. In some aspects, each virtual pressure sensor is in a position in three dimensions relative to the blast source. In some aspects, the method can include generating the weapon signature or obtaining a pre-determined weapon signature for the blast source. In some aspects, the method can include evaluating the accuracy of the blast injury metrics by comparing pressure data of the at least one real pressure sensor with each corresponding virtual pressure sensor.

In some embodiments, a method of generating an anatomical soldier model can include: obtaining a three dimensional skin model; equipping the three dimensional skin model with virtual clothing and virtual protective armor to obtain a virtual soldier model; segmenting the virtual soldier model into different anatomical body regions; articulating segmented virtual soldier model into a pose of a real subject of a blast scene; generating a surface mesh of the articulated segmented virtual soldier model; and generating a report that includes the articulated segmented virtual soldier model and the real subject of the blast. In some aspects, the method can include: obtaining body scan data of the real subject; and generating the three dimensional skin model. In some aspects, the method can include: obtaining anthropometric data for the real subject; and generating the three dimensional skin model using a body model generator. In some aspects, the method can include calculating blast injury metrics for the at least one real subject with the articulated segmented virtual soldier model.

In some embodiments, the soldier model can be modified, such as by: generating an integrated geometry model from the virtual soldier model; obtaining data for anatomically consistent joint locations on the virtual soldier model; creating joint planes at the joint locations; generating intersection loops at the joint locations in order to smooth an intersection between different anatomical regions on the virtual soldier model; generating bounding boxes with faces including the joint planes; segmenting the virtual soldier model into the different anatomical regions based on locations of triangular patches of a surface of the virtual soldier model with respect to the bounding boxes; and articulating the segmented virtual soldier model into a pose of a real subject of a blast scene.

In some embodiments, a method of calculating a weapon signature for a blast source of a weapon can include: obtaining pressure data from a plurality of pressure sensors that recorded pressure during a scene; obtaining topological layout of the plurality of pressure sensors with respect to the blast source; reconstructing scene to place a virtual pressure sensor at a position for each of the plurality of pressure sensors; obtaining time-gated pressure trace data for each of the plurality of pressure sensors; processing the time-gated pressure trace data to obtain a blast wave at the blast source; defining the blast wave at the blast source as a weapon signature for the weapon; and generating a report to include the weapon signature for the weapon. In some aspects, the method can include: obtaining pressure data that is not time-gated; and converting the pressure data to time gated pressure data. In some aspects, the method can include: generating virtual pressure traces from the pressure data that is not time-gated; perform a time shift on the virtual pressure traces to match arrival time of the pressure data that is not time-gated; determine an error between the virtual pressure traces and the pressure data; and determine whether or not the error is acceptable. If the error is acceptable, then method includes using the virtual pressure traces. If the error is not acceptable, then the method includes modifying blast wave kernel data and generating new virtual pressure traces for time shifting and error determination.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIGS. 16A-16D include graphs that show comparisons between FPS predicted and IPS optimized pressure traces collected at a virtual location (chest) for all four human subjects.

DETAILED DESCRIPTION

Figure 1:
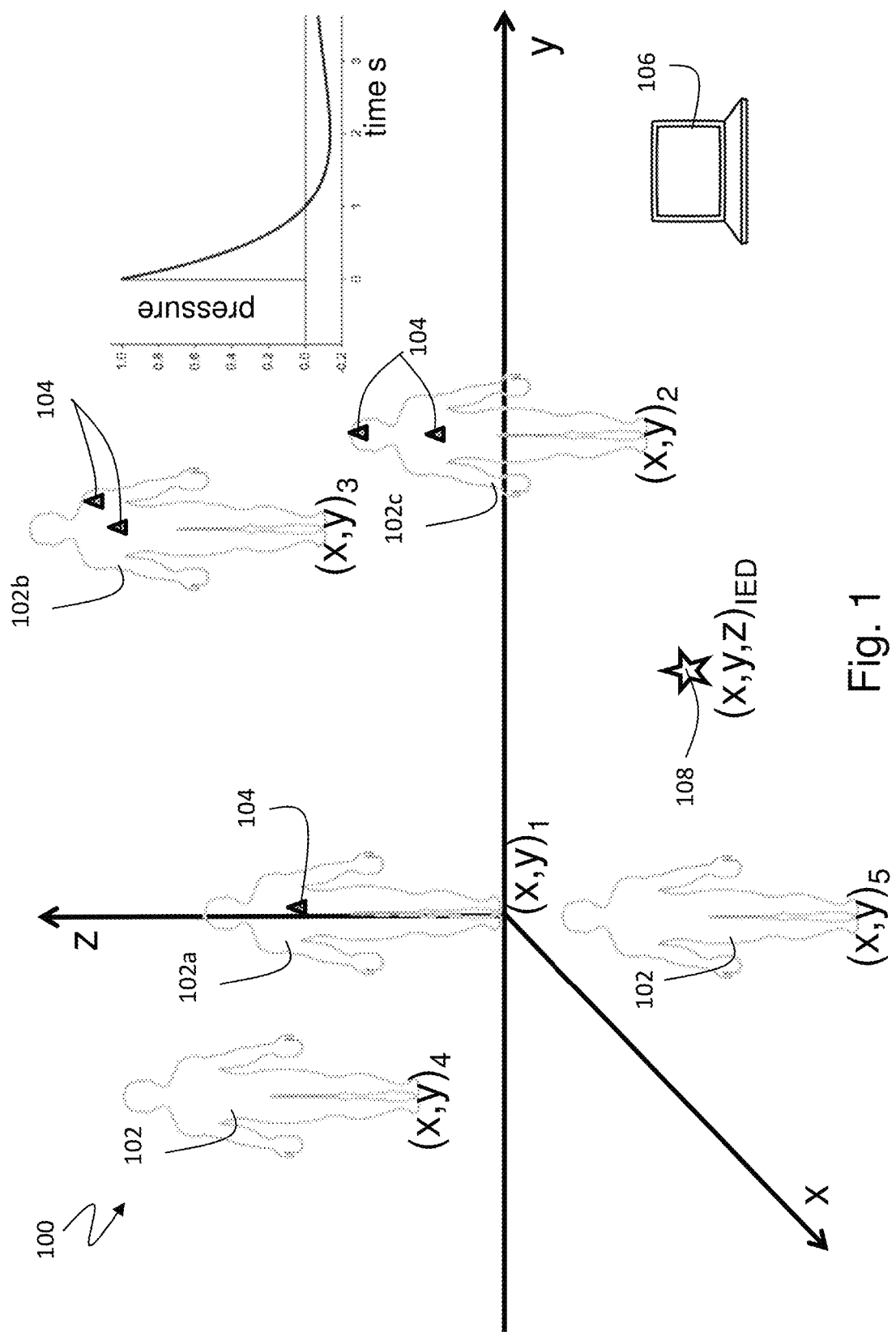
FIG. 1 includes a schematic diagram of an IED blast scene showing the location of the IED, positions of individual human subjects exposed to the blast wave and locations of wearable pressure sensors on some of the subjects.

In the following detailed description, reference is made to the accompanying drawings, which form a part hereof In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology provides a system and method that can quickly identify the location of an explosion source. The system and method can facilitate the collection and analysis of forensic evidence after an explosion (e.g., bomb blast), and provide a better understanding of lethality, survivability, and protection for explosions. The system and method can be used to perform a detailed analysis of an explosion (e.g., IED explosion), and then model the explosion in order to predict the blast output force at different locations away from the exposition in order to predict injuries that may occur to humans based on the blast location and power. This can allow the system and method to determine the blast loads on a human that has been affected by the blast in order to determine blast loading at specific anatomical locations of that human, or to simulate blast loads on a model human by the blast in order to predict possible blast loading at specific anatomical locations of that model human. As a result, injuries to various body parts, such as the brain, may be determined or predicted based on the analysis of the explosion. The information obtained during the methods can be compiled and included in a report regarding the data, such as any data described herein. The report can than be provided to an entity, such as military or medical professionals or subjects in the blast. The information in the report can information regarding the blast and/or information regarding the injuries. The report can be provided electronically or as a hard copy. The report, or data thereof, may also be saved in a database for future analysis, use, or reporting.

In some aspects, the system and method include at least one pressure sensor, preferably two pressure sensors, and a computing system configured with computer-executable code that when executed by a processor causes the computing system to analyze pressure sensor data and compute an explosion location and explosive mass (e.g., charge mass) from pressure sensor data. The pressure sensor data can be processed by the computing system for automated reconstruction of the explosion blast and blast wave loading on humans with a blast zone based on pressure sensor data. In an example, the system utilizes data collected by the pressure sensors outfitted on human subjects or equipment (e.g., vehicle) as inputs to an inverse problem solver in order to calculate the location and charge mass of an explosive device and detailed pressure loads on human bodies exposed to the blast wave. The results of the disclosed system could be used for forensics and for calculation of blast wave loads on the whole human body and on specific organs such as head and torso. The results and information obtained may be included in the reports described herein.

In some embodiments, the system can include wearable pressure sensors, which can be worn by persons, such as military personnel or on equipment (e.g., vehicles). The sensors may be mounted to the human body at one or more locations (e.g., near ears, eyes, head, chest, arms, etc.) or embedded in equipment (e.g., backpack, helmet, body armor, watch, communication device, phone, walkie-talkie, glasses, sunglasses, eye protection, etc.) worn on the human body. The pressure trace data from such pressure sensors can be used to reconstruct the location of the explosion, the explosive mass, and the blast load profile on human subjects. Accordingly, the computing system can process the pressure trace data in order to reconstruct an explosion (e.g., IED) blast event and then reconstruct loads on human bodies by the explosion based on the pressure sensor data. In a first step of the computational protocol, an inverse problem solver (e.g., available in CoBi tools) is used to process the pressure sensor data to identify an explosion (e.g., IED) location and explosive charge mass. In a second step, the reconstructed blast wave provides initial conditions for a computational model to be created and used (e.g., CoBi) to calculate blast loads on human bodies affected by the explosion. For example, the first step can be useful to identify the location and explosion charge mass of an improvised explosive device (IED) event to assist an investigation by a law enforcement team. In another example, the second step can be useful for medical personnel by providing them with predictions of impacts of blast wave loads on a human at various locations of the human anatomy, and thereby allow for a medical professional to perform injury assessment on the subject for assessing injuries at various human anatomy locations. In a specific example, the predicted blast wave load on the human anatomy can be used for a diagnosis of blast wave traumatic brain injury (TBI), for which typically there are no visible wounds and the physiological and cognitive symptoms become apparent hours, days, months and sometimes years after the blast exposure. Now, the TBI may be predicted based on the model of the blast wave, which blast wave was calculated using the inverse problem solver (e.g., first step).

In some embodiments, the CoBi tools suite (CFD Research Corp.—CFDRC website) can be used in the methods described herein.

In some embodiments, the methods can include receiving pressure sensor recordings into the computing system from the pressure sensors, and then to reconstruct the explosive blast event based on the pressure sensor recordings. The pressure sensor recordings can be provided to the computing system as pressure signals from one, or preferably two spatially distributed pressure sensors. While one pressure sensor may be used in the protocols, more accurate blast reconstruction may be achieved by at least two spatially distributed pressure sensors. The pressure data can then be processed with the computer to calculate a blast wave caused by an explosion, and thereby the explosion can be reconstructed such that the blast location and blast charge mass can be determined (e.g., calculated or estimated).

In some aspects, the pressure data from two or more pressure sensors worn by individual people or equipment (e.g., a vehicle) can be used as inputs to a computational algorithm, referred to as the inverse problem solver (IPS), which is processed by the computing system in order to reconstruct the location of the explosion center and to compute the dynamics of the blast waveform. The results of the IPS are then processed by the computing system with a blast model to conduct forward problem solver (FPS) simulations to compute space-time resolved blast wave loads on blast wave exposed humans and equipment.

For military applications, the system and method can collect relative proximity information between sensors (e.g., on one soldier and/or on multiple soldiers and/or on one or multiple objects, such as vehicles). In one aspect, multiple soldiers can each wear one or more sensors. In some aspects, the sensors can be strategically placed over a soldier's body in two or more anatomical locations to monitor the relative difference of the blast waveform at the different anatomical locations. Then, the computing system can process the recorded sensor data using an optimization algorithm to identify the blast threat, such as blast charge mass and blast location relative to the soldier.

The systems and methods can also be used to determine blast wave exposure on human bodies during military training of personnel exposed to blast and shock waves. This can include breachers, snipers, artillery crew, deminers, and others wearing one or more sensors during the ordinary course of action with their equipment so that the pressure loads they receive can be recorded by the sensor and proved to the computing system for analysis to reconstruct the blast waveform to identify the blast location and blast charge mass, and then to determine the loading they experience at different anatomical locations. The results of such blast loading reconstruction simulations on the soldiers can be used to correlate these with blast injury probability using experimentally collected "dose-response" data, [Gupta and Przekwas 2013]. As such, after the blast loading at different anatomical locations is determined, this information can then be processed to determine or predict injuries to various organs, such as the brain. This information (e.g., report) can then be used for a myriad of purposes ranging from designing better protective equipment, determining whether or not the soldier should receive rest without exposure to blasts and from a certain timeframe thereof, determining medical treatment that should be received, determining protocols related to blasts, and/or improving emergency response to blast events or others.

In some embodiments, the method can be automated. This can include the sensors being communicatively coupled during or after the explosion blast event, and once communicatively coupled or once receiving an input command from a user, the computing system performs an automated reconstruction of explosion blast and blast wave loading on humans using pressure traces data from two or more sensors.

In some embodiments, the computing system processes the pressure traces data, in the form of pressure versus time, that are collected by two or more sensors located on human subjects or equipment. The pressure traces data from two or more pressure sensors are processed by the IPS to calculate the location and charge mass of an explosive device. The sensors can be located on one person, on multiple people and on equipment or buildings.

In some embodiments, a reference x-y-z coordinate system (z- is the vertical direction) can be chosen to position people, both those who wear sensors and those who don't in the coordinate system so that the location of the explosion can be determined in the coordinate reference system. This can facilitate the modeling and determinations. Approximate anthropometric information, body position in the x-y space and body orientation and posture can be obtained from information or determined by the computing system. In some aspects, the protocols can include obtaining the sensor location(s) on the body or in the coordinate system, which are then processed during the protocols.

In some aspects, the human anthropometric data are used to generate more accurate 3D body surface geometry during the protocols. In some aspects, at least one, two or three anthropometric parameters, such as body height, weight and gender can be used as inputs to a body anatomic geometry generator [Zhou et al 2016]. Additional measurements, such as torso circumference, extremity lengths, body mass index, body part volume, or other physiological information can be used to improve the resolution accuracy of the subject specific anatomy geometry of a person. If a body scan of a subject is available, it can be used directly as input into the computing system for the protocols. A scene generator computation [Zhou et al 2016] can be used to arrange one or more human body positions in the x-y space of the coordinate system, with specific orientations and articulations of individual human bodies and body parts.

Additionally, data from more sensors results in higher accuracy of the IPS explosion blast reconstruction step. In the field, there may only be sensors on the personnel or equipment. In training or test situations, data from pressure sensors located on equipment, buildings, embedded in the environment, in text mannequins, can be used along with buildings surface geometry or other environmental surface geometry can also be used as inputs for IPS blast reconstruction. The IPS simulation computations use a mathematical model of blast wave dynamics and parameter optimization algorithm to calculate the x-y-z location of the explosive device (e.g., IED) and the explosive mass. Positions and orientations of human bodies relative to the IED blast explosion location are either known and used as input or calculated, such as by the scene generator.

In some embodiments, results of the IPS simulations are subsequently used as inputs for FPS simulations to predict space-time resolved blast wave loads on human bodies and equipment exposed to the blast wave. Blast loads can be calculated on any human body and equipment exposed to a blast wave, either wearing a pressure sensor or not. The FPS simulations can be used to generate pressure traces by virtual sensors located on computational models of actual or virtual humans (e.g., human model). Comparison of pressure traces collected from physical sensors and virtual sensors can be used to evaluate the accuracy of the IPS reconstruction model.

In some embodiments, results of FPS simulations can be used to calculate space-time pressure loads on the entire human body or selected portions thereof, whether internal or external, that may be exposed to the blast wave. Examples of selected portions can include body organs, such as head/brain and torso/heart/lungs or other. These results can be used to calculate injury parameters, such as by the Head Injury Criteria (HIC) [Marjoux et al 2008, Hutchinson 1998, Gupta and Przekwas 2013] or Chest Wall Velocity Predictor [Axelsson and Yelverton 1996, Przekwas 2008], which can help in injury diagnostics, treatment, prevention, and care (e.g., long term care, time away from blast exposure, etc.).

In some embodiments, the IPS results can identify the location of the blast. This can allow military or other personnel to identify possible other locations for explosion sources, which may become more and more critical for implementing anti-terrorist activities.

FIG. 1 shows a system 100 that can be used in the method for automated reconstruction of explosion blast events using the IPS, and calculation blast wave loads on humans 102 using the FPS. The humans 102 are shown as having wearable pressure sensors 104 that provide pressure sensor data to a computer 106 for computer processing as described herein (e.g., IPS, FPS, etc.). The humans 102 are in a coordinate system, which can be arbitrary, or with a center at a specific human 102a or at the blast location. Initially, the blast scene involves an IED 108 of unknown mass and unknown location and one or several humans 102 exposed to the blast. FIG. 1 provides a schematic of the IED blast scene showing the location of the IED 108, positions of individual humans 102 (e.g., subjects) exposed to the blast wave and locations of wearable pressure sensors 104 on some of the humans 102. The center of the x-y-z coordinate system is arbitrarily placed at the position of a selected individual human 102. Positions of all other humans (x,y, z=0) are known or estimated or calculated, but the location of the IED 108 (e.g., x,y,z coordinate) is unknown. The IED 108 can be located on or above the ground. A first human 102a is shown to have a sensor 104 on their chest. A second human 102b is shown to have a sensor 104 on their chest and a sensor 104 on their shoulder. A third human 102c is shown to have a sensor 104 on their chest and a sensor 104 on their head. The sensors 104 can be configured with a transmitter that can transmit (e.g., wirelessly, wired, optical or other) the pressure sensor data to the computer 106 for storage on a memory device and for processing in the protocols described herein (e.g., IPS, FPS, etc.). Correspondingly, the computer 106 can include a communications module, such as a transceiver that allows for the receipt of the pressure sensor data, and may also allow for transmitting information, such as the results to another computing system, through the Internet, or other transmission. In some instances, such as unknown blast situations, the pressure sensor data may be saved in the sensors 104 and then input into the computer 106 at some point after the blast, such as during a forensic investigation. In some other instances, such as a controlled or test scenario, the sensors 104 can include transmitters that transmit the pressure sensor data to the computer 106 in real time or at time period intervals. In any event, the sensors 104 provide the pressure sensor data to the computer 106.

Figure 2:
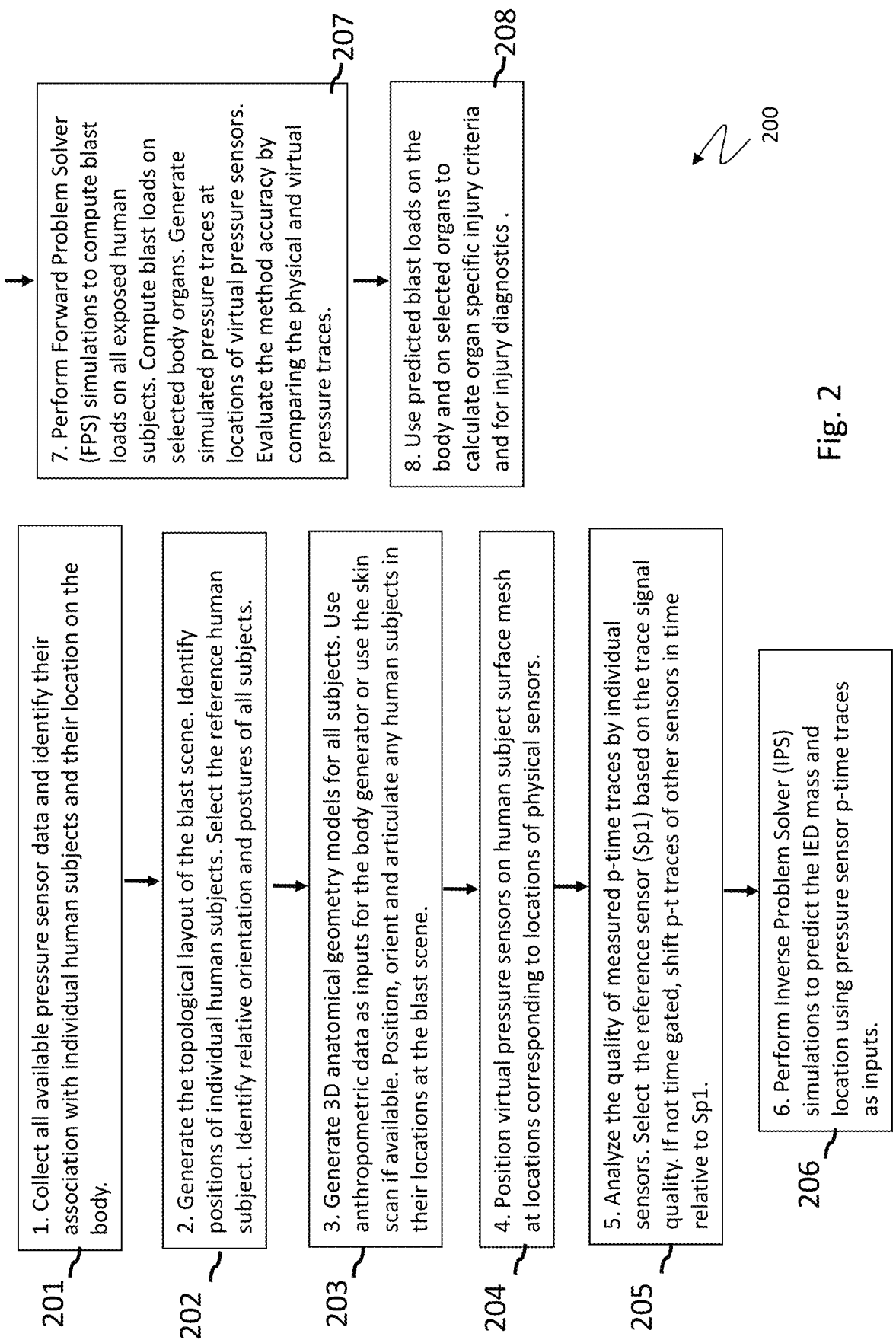
FIG. 2 includes a flow chart showing steps of the process of the disclosed system and method for the reconstruction of an explosion blast event and calculation blast wave loads on human subjects.

An example of the main data processing protocol is provided in FIG. 2. The system 100 uses available pressure traces from wearable pressure sensors 104, generates the topological layout of the blast scene with the computer 106, and anatomical geometries of human bodies 102 where some of whom may have wearable pressure sensors 104 and some may not. The quality of the pressure traces from the system 100 is analyzed and time-aligned.

FIG. 2 shows the method 200 that can include the following steps. Step 1 includes collecting all available pressure sensor data, and identify the association of the pressure sensors with individual human subjects and the location of the pressure sensors on the human body of each subject (block 201). Step 2 includes generating the topological layout of the blast scene, identifying positions of individual human subjects, selecting the reference human subject (e.g., for the coordinate system), and identifying relative orientation and postures of all subjects (block 202). Step 3 includes generating 3D anatomical geometry models for all subjects, using anthropometric data as inputs for the body generator or use a skin scan if available, and positioning, orienting and articulating any human subjects in their locations at the blast scene (block 203). Step 4 includes positioning virtual pressure sensors on a human subject surface mesh at locations corresponding to locations of physical sensors (block 204). Step 5 includes analyzing the quality of measured p-time traces by individual sensors, selecting the reference sensor (Sp1) based on the trace signal quality, and if not time gated, shift p-t traces of other sensors in time relative to Sp1 (block 205). Step 6 includes performing calculations of data with the Inverse Problem Solver (IPS) simulations to predict the IED mass and location using pressure sensor p-time traces as inputs (block 206). Step 7 includes performing Forward Problem Solver (FPS) simulations to compute blast loads on all exposed human subjects, computing blast loads on selected body organs, generating simulated pressure traces at locations of virtual pressure sensors, and evaluating the method accuracy by comparing the physical and virtual pressure traces. Step 8 includes using predicted blast loads on the body and on selected organs to calculate organ specific injury criteria and/or for injury diagnostics. Accordingly, IPS simulations can be used to predict the IED mass and location (block 206) and are used by subsequent FPS simulations (block 207) to calculate blast wave loads on human subjects (block 208).

To reconstruct the IED blast scene and to compute blast loads on exposed human subjects, the computing protocols can use three simulation algorithms: 1) generation of 3D anatomical geometry of human subjects involved in the blast scene, such as shown in FIG. 1, using anthropometry data as inputs; 2) processing the Inverse Problem Solver (IPS) for prediction of IED charge mass and location using data from wearable pressure sensors as inputs processing; (3) processing the Forward Problem Solver (FPS) for fast modeling of blast wave dynamics and blast wave loading of humans and surfaces using IED mass and location obtained from IPS simulations. The data from the wearable pressure sensors are used as inputs, and software tools are used for optimization-based parameter calibration. All three algorithms are described herein.

Accordingly, FIG. 2 provides the flowchart showing the main steps of the process of the disclosed system and method for the reconstruction of an explosion blast event and calculation blast wave loads on human subjects. The disclosed method uses pressure traces data from two or more sensors and the inverse problem solver (IPS). The IPS results are then used as inputs to the forward problem solver (FPS) simulations to compute space-time resolved blast wave loads on blast wave exposed human subjects.

Figure 3:
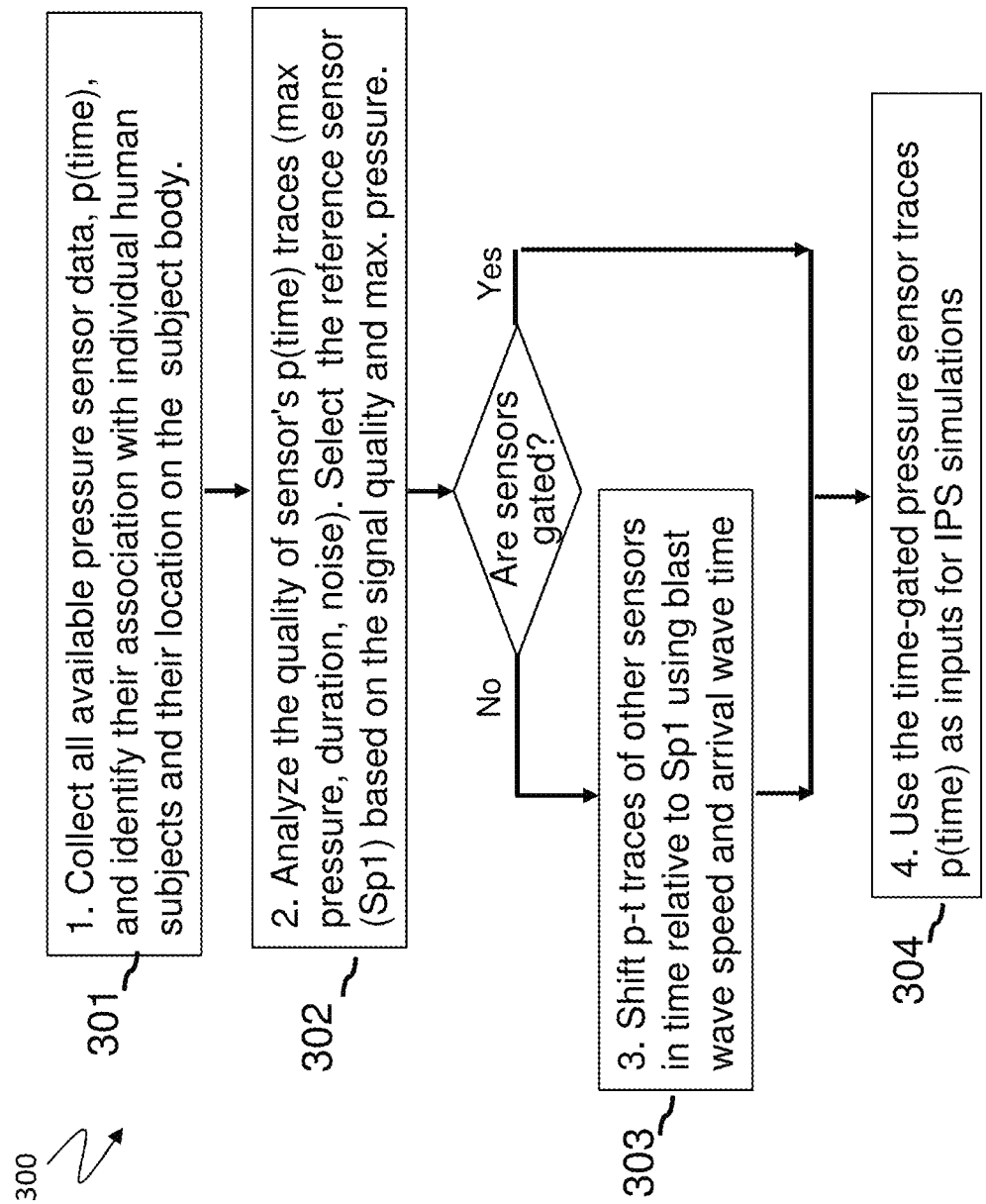
FIG. 3 includes a flow chart showing steps in the collection, analysis and processing of sensor collected pressure traces.

FIG. 3 provides a method 300 for the steps that are followed for collection, analysis, and processing of sensors collected pressure traces. For non-time gated sensors time shift relative to the reference sensor is performed. Step 1 includes collecting all available pressure sensor data, such as p(time), and identify their association with individual human subjects and their location on the subject body (block 301). Step 2 includes analyzing the quality of the sensor p(time) traces (e.g., max pressure, duration, noise, etc.), and selecting the reference sensor (Sp1) based on the signal quality and maximum pressure (block 302). After step 2, there is a decision for determining whether or not the sensors are gated. If no, then step 3 is performed, which includes shifting p-t traces of other sensors in time relative to Sp1 using the blast wave speed and arrival wave time (block 303). If yes, then step 3 is skipped and the method 300 moves to step 4, which includes using the time-gated pressure sensor traces p(time) as inputs for IPS simulations (block 304).

Figure 4:
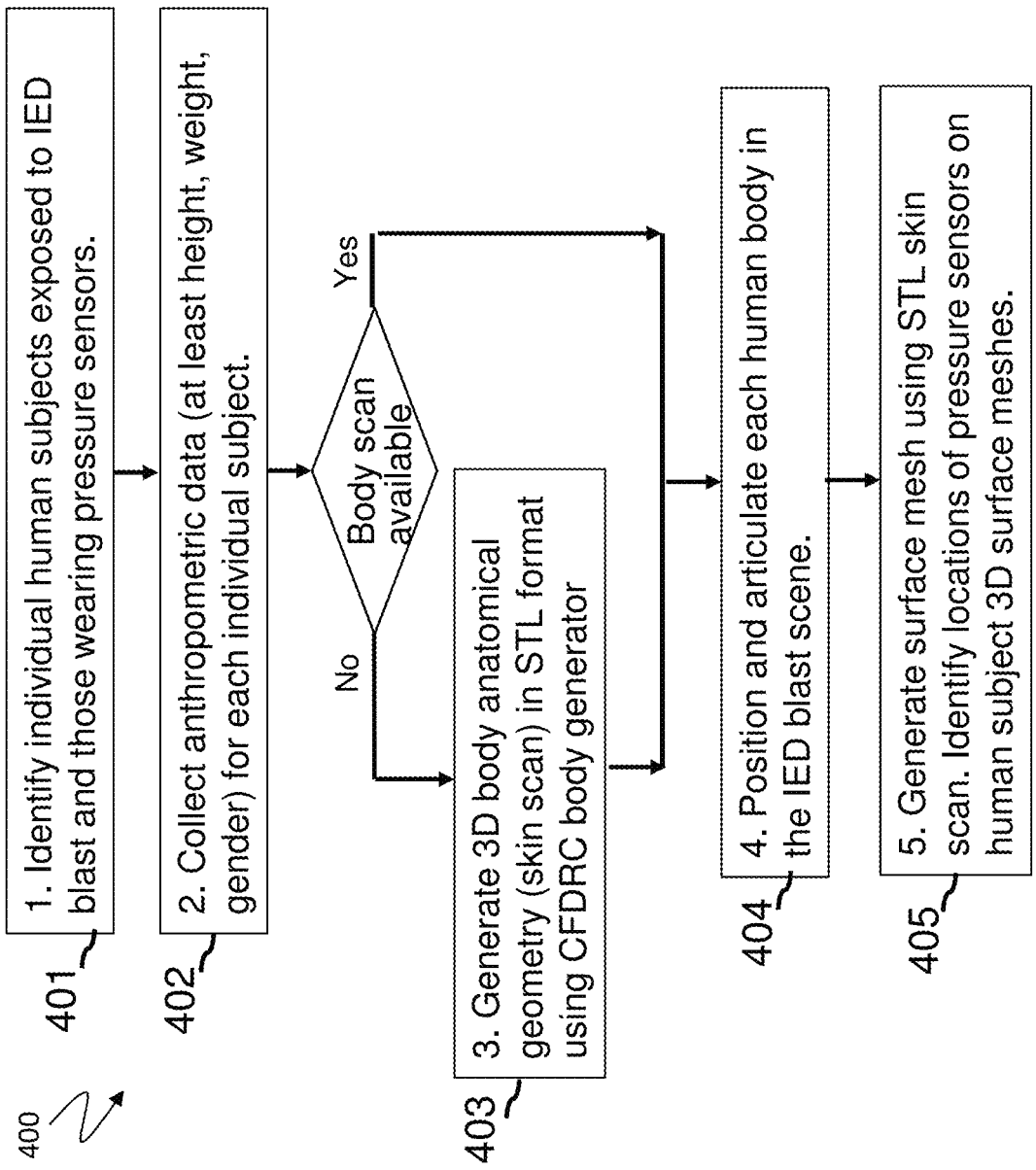
FIG. 4 includes a flow chart showing the main steps in the generation of the IED blast scene involving all human subjects.

FIG. 4 includes a flowchart for a method 400 for generation of the IED blast scene involving all human subjects. Here, basic anthropometric data are collected as inputs for generation of 3D human subject body models. If body skin scan data is available, it can be used directly to generate 3D body surface mesh. Otherwise an anthropometry-based 3D body generator is used to create 3D body surface mesh. Step 1 includes identifying individual human subjects exposed to the IED blast and those human subjects wearing pressure sensors (block 401). Step 2 includes collecting anthropometric data (e.g., at least height, weight, gender) for each individual subject with or without a pressure sensor (block 402). After step 2, there is a decision for determining whether or not a body scan is available. If no, then step 3 is performed, which includes generating 3D body anatomical geometry (e.g., skin scan) in STL format using a body generator computation (block 403). If yes, then step 3 is skipped and step 4 is performed, which includes positioning and articulating each human body in the IED blast scene with the computer modeling (block 404). Step 5 includes generating surface mesh data for one or more of the human bodies using an STL skin scan, and identifying or determining or estimating locations of virtual pressure sensors on human subjects' 3D surface meshes (e.g., which are virtual humans) (block 405).

Accordingly, the method can include generating human body models and the IED blast scene. The simulation of blast wave interaction with human subjects involves generation of geometry and computational mesh data for the blast scene and for individual human subjects. Any computer aided design (CAD) tools that utilize geometry can be used to set up the IED blast scene and to identify coordinate (x, y, z=0) positions of human subjects in the scene, such as shown in FIG. 1. The human body anatomic generation and articulation algorithm, shown in FIG. 4, can be processed using basic human body anthropometric measurements (block 401, block 402) and generates 3D human body surface geometry in STL format (block 403). The human body is then positioned in the blast scene (block 404) and articulated to the specific posture (block 405) for the blast event simulations. In an example, the method can use body generator tools to generate geometry/mesh models of individual human subjects [Zhou et al 2016]. The human body is represented in the form of a surface mesh (e.g., triangles, quads, or other surface representation) which is then used to calculate the blast wave interaction with the body (block 405).

The extraction of blast parameters, such as the explosion mass weight and location, from pressure sensor data can be performed using an error optimization algorithm to find optimal sets of model coefficients. In general, the error optimization problem requires two fundamental pieces of information: experimental measurements and a theoretical model with adjustable coefficients. The experimental measurements are generally available at discrete time points; {d1, d2, . . . , dN}, where di (i=1, 2, . . . N) is the experimental measurement taken at time ti. The theoretical model, f(t, p), contains a set of linearly independent model coefficients {p1, p2, . . . , pM}, and is able to predict the variation in the measured value with time.

In some embodiments, there are at least three different optimization methods, which can be implemented in CoBi tools, to predict explosion center and explosion mass weight. The IPS can include a "forward" flow field solver and an optimization algorithm. The forward problem flow field solver, using input from an optimization algorithm, performs flow simulations to produce medium pressure, velocity, temperature and species concentration and so on. The optimization algorithm uses the computed flow data and measured data from the sensors, in which measured data are called set point values, to perform error optimization calculation to generate new input for the flow field solver. This iteration procedure finally gives optimized quantities whose error with set point values is minimized. When forward simulations are conducted using 3D high fidelity blast wave propagation and pressure loading on a human body, large computational resources (e.g., parallel computing systems, long simulation times) are required. In this work, for forward simulations, the processing can use a reduced order fast running blast wave model available in the CoBi tools.

The FPS can be used for modeling blast loads on the humans (e.g., virtual humans) in the blast zone. Computational modeling of blast wave loading on a human body, referred to as a FPS, can be conducted using either high-fidelity 3D computational fluid dynamics tools [Wiri and Needham 2016, Wiri et. al. 2017, Gupta and Przekwas 2013] or approximate, fast running blast simulation software such as CONWEP [Kingery, 1984, CONWEP, 1993]. However, for IPS simulations, involving a very large number of FPS simulations in an optimization loop are not practical.

Figure 5:
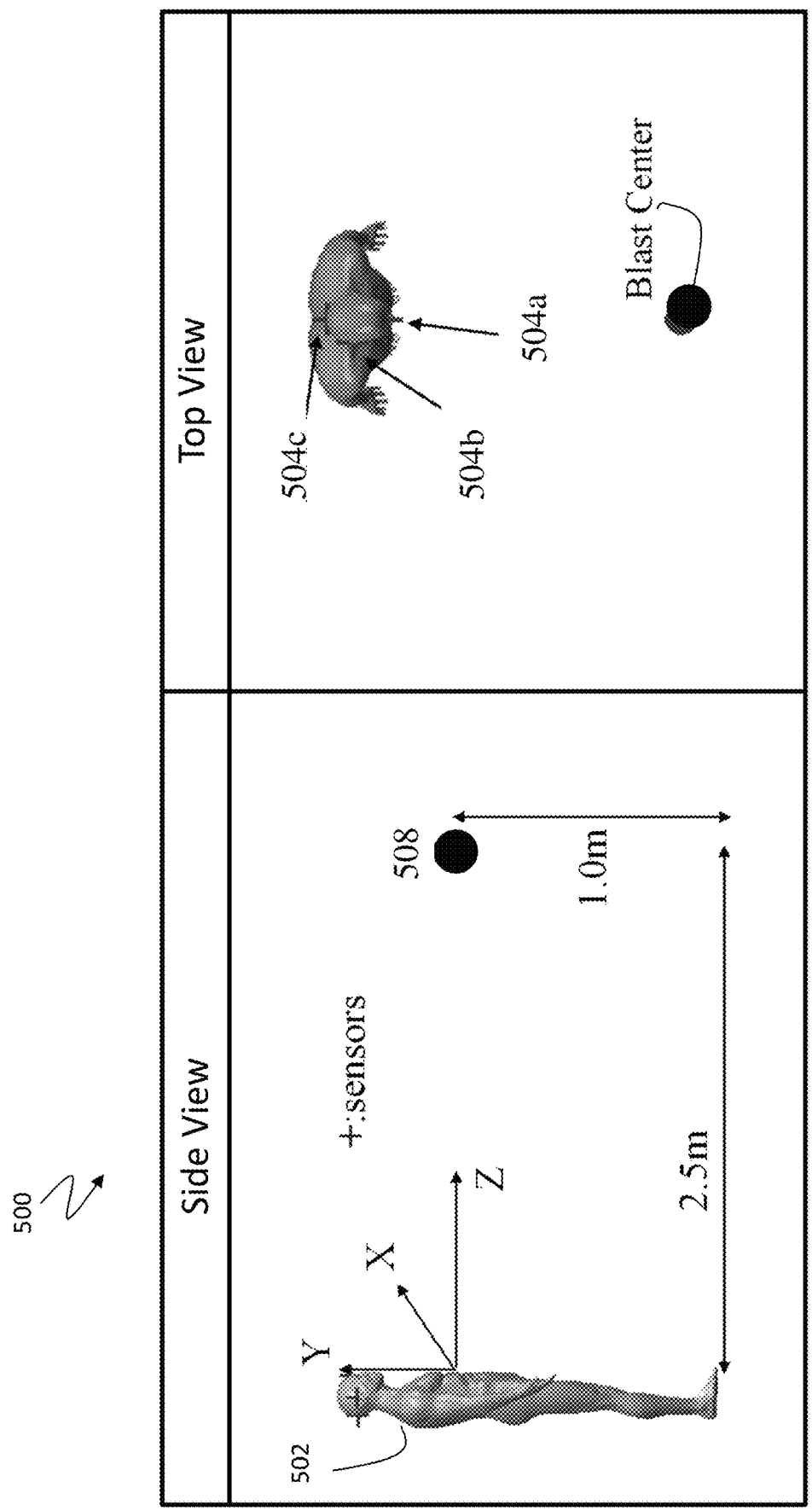
FIG. 5 includes a schematic diagram showing an example blast scene involving an IED located above the ground and a human subject facing the IED.
Figure 6:
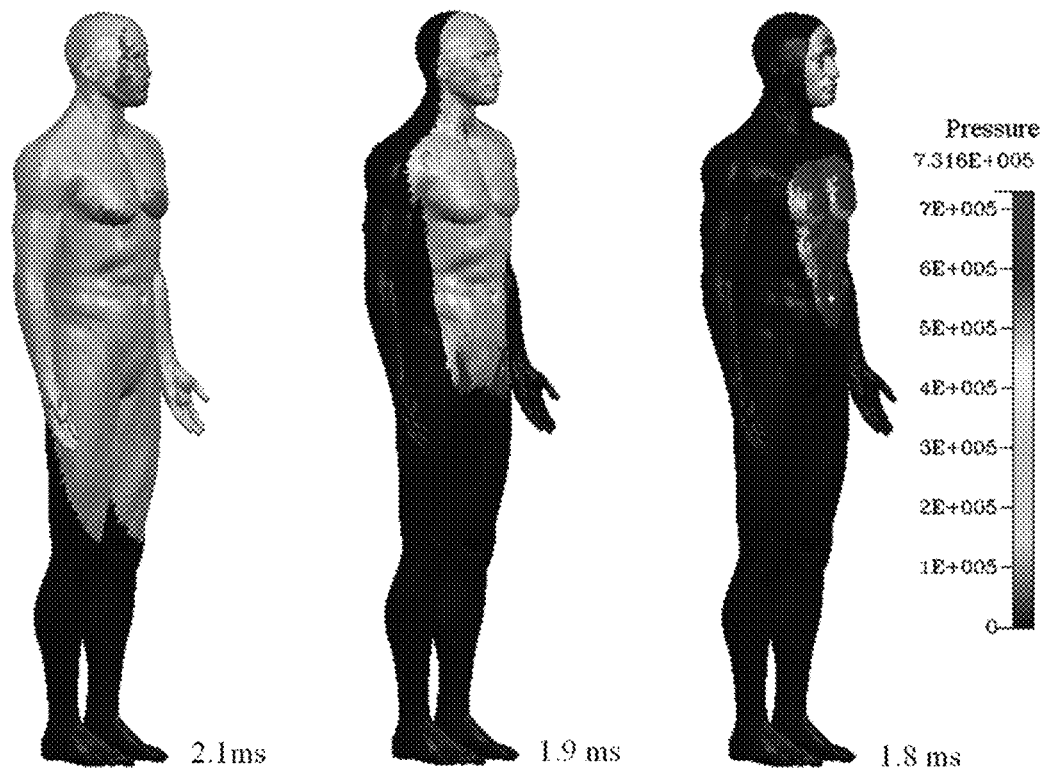
FIG. 6 shows FPS simulation results for the example blast scene of FIG. 5, and predicted blast wave loads on a human body at three time-instances during blast wave propagation around the human body.
Figure 7:
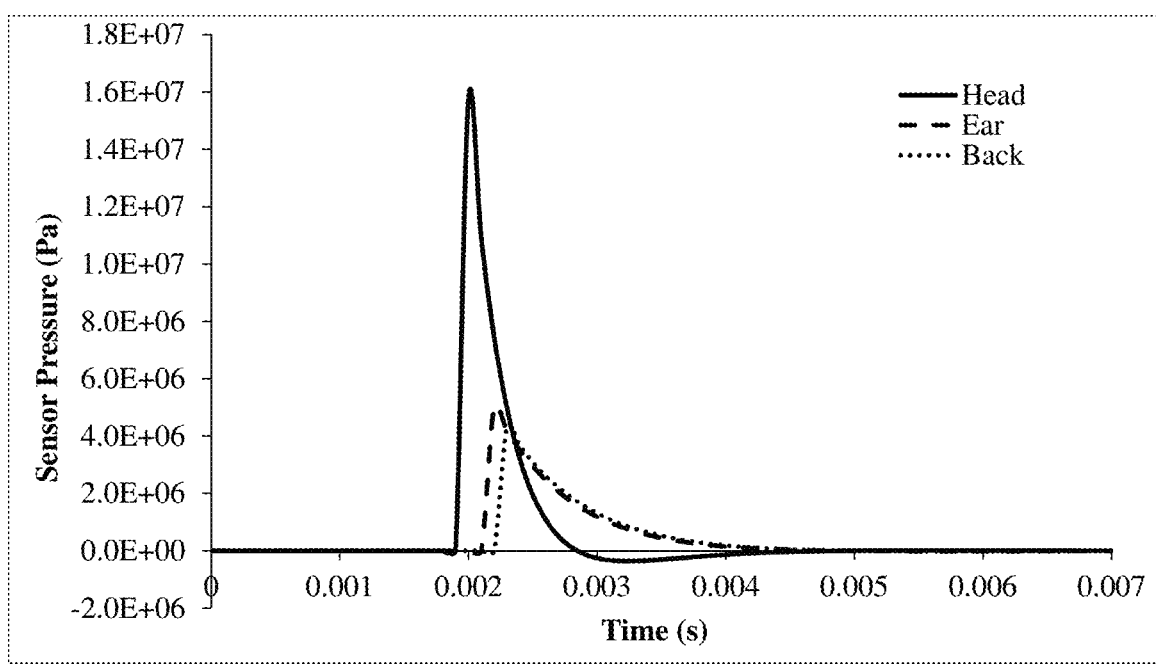
FIG. 7 includes a graph showing calculated pressure traces at three locations on the human head using FPS simulations for the example blast scene of FIG. 5.

In some embodiments, the computer processing can utilize approximate fast running tools, similar to CONWEP (e.g., calculates range of blast effects from different types of high explosives), but with the capability to calculate blast wave refection (e.g., off the ground), and wave diffraction on objects, such as the human body. The processing can use fast running blast wave dynamics models implemented in the CoBi tools for both FPS and IPS simulations. In some embodiments, other blast wave gas dynamics, including CFD tools (CFDRC website) can be used. However, the processing has been demonstrated with CoBi tools for FPS simulations on a virtual IED blast scene, which is shown in FIG. 5. For example, a virtual human subject wearing virtual pressure sensors at the forehead, ear and back of the head is positioned at 2.5 meter from an explosive device placed 1 meter above the ground. An analytical model of physics of explosive charge detonation is used to establish initial post-detonation spherical shock wave kernel (i.e., blast wave kernel). Then, the CoBi FPS blast dynamics tools are used to simulate blast wave propagation away from the detonation point toward exposed human subjects and blast wave interaction with the human body, such as shown in FIG. 6. The FPS simulations also generates virtual pressure traces at virtual sensor locations, such as shown in FIG. 7. As described below, the FPS predicted virtual pressure traces can be used to validate the IPS tools.

FIG. 5 includes a diagram showing a side view and a top view of an example blast scene 500 involving an IED 508 (e.g., blast center) located above the ground and a human subject 502 facing the IED 508. Three human subjects 502 are wearing three virtual pressure sensors that are placed on the human forehead (e.g., forehead sensor 504a), ear (e.g., ear sensor 504b), and the back of the head (e.g., back of head sensor 504c) to record virtual pressure traces using FPS simulation results. The analysis can include the use of the inverse problem solver in the CoBi tools to reconstruct the IED blast event using distributed human wearable pressure sensor data. A whole human body geometry and an IED explosive charge mass are shown in FIG. 5. The charge location (x, y, z) coordinates are known. In some embodiment, the human subject 502 is a human manikin that carries the three pressure sensors 504a,b,c on the front side near the right ear and back of the head respectively. In order to test the inverse problem solver, the protocol assumes the explosive charge to be 5 lbs of C4 dynamite and performed a forward blast simulation using CONWEP fast blast simulation software (Kingery, 1984, CONWEP, 1993) to create IED blast pressure data on all sensors, and a graph can be generated as shown in FIG. 7.

FIG. 6 shows the FPS simulation results for the example blast scene (e.g., FIG. 5), and predicted blast wave loads on a human body at three time-instances (e.g., 1.8 ms, 1.9 ms, and 2.1 ms) during blast wave propagation around the human body. Going from right to left, it can be seen that the lighter portion is higher pressure that spreads and increases over the time period.

Table 1 lists the explosion mass optimized by the LM method, DAKOTA and Shooting method, which are described in more detail herein. The data shows that the LM method failed because the LM method could not calculate pressure gradient for this dramatically changed pressure signal at sensors. The DAKOTA software also produced an explosive mass with large error since DAKOTA also needs to calculate gradient of blast pressure field. The Shooting method gives excellent results, the true value is 5 lbs. and the Shooting method predicts as 5.006 lbs.

TABLE 1

Predicted IED Blast Charge Mass

| Explosive Mass (lb.) | True Value | DAKOTA | Shooting | LM |
|---|---|---|---|---|
| m | 5 | 7 | 5.006 | Failed |

FIG. 7 includes a graph that shows the calculated pressure traces at three locations on the human head using FPS simulations for the blast scene shown in FIG. 5.

Figure 8:
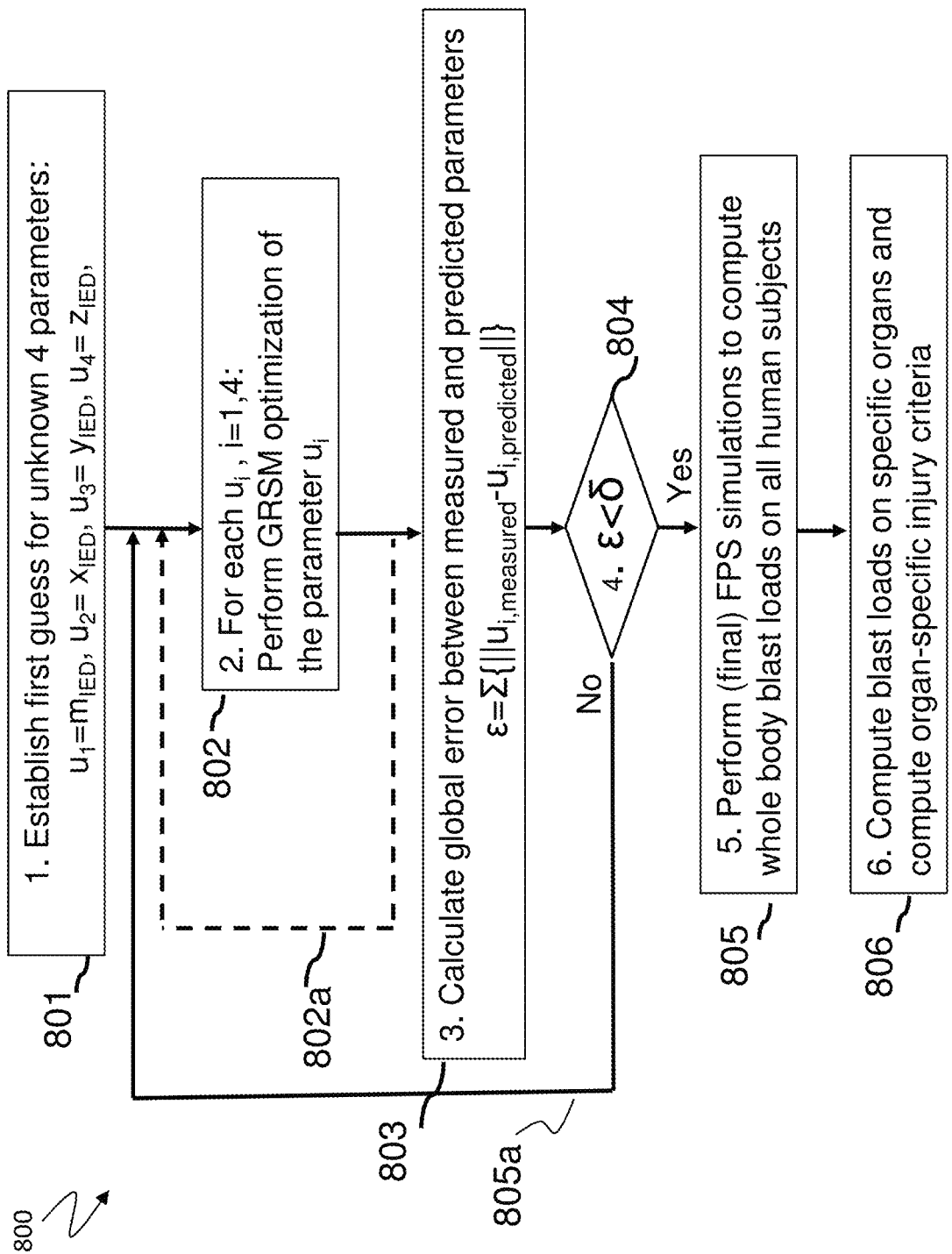
FIG. 8 includes a flow chart that shows the inverse problem solution (IPS) algorithm and calculation of blast loads on human subjects using forward simulations (FPS).

The IPS is used to reconstruct the IED blast event scene using pressure sensor data as inputs to optimization-based iterative IPS simulation algorithm. FIG. 8 provides an example algorithm 800. Step 1 includes establishing a first guess for unknown 4 parameters: $u_1=m_{IED}$, $u_2=x_{IED}$, $u_3=y_{IED}$, and $u_4=z_{IED}$ (block 801). Step 2 includes performing Golden Ratio Shooting Method (GRSM) optimization of the parameter $u_i$ for each $u_i$, i=1, 4 (block 802). The back loop 802a shows each iteration for each $u_i$. Step 3 includes calculating the global error between measured and predicted parameters—$\varepsilon=\Sigma\{\|u_{i,\ measured}-u_{i,\ predicted}\|\}$ (block 803). Here, measured can be from experiments and predicted can be from calculations. Then, step 4 is a decision as to whether or not $\varepsilon<\delta$ (block 804). If not, then a back loop goes back to step 2. If yes, then step 5 is performed, which includes performing a final FPS simulation to compute whole body blast loads on all human subjects (block 805). Step 6 includes computing blast loads on specific organs, and then computing organ-specific injury criteria for the human subjects. This can allow for an estimation or prediction of the injury to specific organs in the subject, such as the brain. Then, the information can be used to create a treatment plan for the subjects based on the determined blast loading on the specific organs.

The methodology provides a fast and robust optimization tool that is used in the IPS simulation algorithm. In the present embodiment, the GRSM optimization algorithm can be used for parameter optimization in algorithm 800 [Kiefer 1953, Avriel 1966]. The GRSM is used with the IED charge mass and the IED x-y-z position as optimization parameters, denoted by vector $u[m_{IED}, x_{IED}, y_{IED}, z_{IED}]$. The $\varepsilon(u)$ denotes the least square error between the simulated and measured physical parameter, and u and $u_{LB}$ and $u_{UB}$ denote lower and upper bounds of the specific parameter (component of vector u), which is shown in the graph of FIG. 9.

In some embodiments, the optimization algorithm used for the disclosed method involves the following iterative steps for each of the u parameters: (1) evaluate system least square error $\varepsilon(a)$ between the simulated and measured data at the lower bound, $u_{LB}$, and the upper bound $u_{UB}$; (2) Randomly pick third input parameter $_{u1}$ for obtaining the model error $\varepsilon(u_1)$ between the simulated and measured data; (3) If $\varepsilon(u_1)\leq\varepsilon(u_{LB})$, then the next guess parameter $u_2$ is located between ($u_1$, $u_{UB}$), otherwise i.e., if $\varepsilon(u_1)\leq\varepsilon(u_{LB})$, the next guess parameter $u_2$ is selected between ($u_{LB}$, $u_1$); (4) Define non-dimensional parameter $\xi=(u-u_{LB})/(u_{UB}-u_{LB})$, ($0\leq\xi\leq1$), the new parameter is calculated either by mean value $\xi_2=0.5(\delta_1+1)$ or golden ratio $\xi_2=0.5(\sqrt{5}-1)(\xi_1+1)=0.618(\xi_1+1)$; and (5) Continue the steps (3) and (4) until finding the desired match between measured and predicted u parameters. Once convergence is achieved with algorithm 800, the predicted parameters, IED charge mass and location, are used as initial conditions for the final FPS simulation to compute blast wave propagation and loading on exposed human subjects. In the final step, blast loading on specific organs, such as head, torso, extremities, are computed and used to calculate organ specific injury criteria. The blast loads on the whole human body can be used to conduct human body biodynamic simulations [Tan et al 2011].

Accordingly, algorithm 800 shows the use of the IPS and calculation of blast loads on human subjects using the FPS. FIG. 8 shows the main steps of the inverse (IPS) and forward (FPS) simulation algorithm. For the IPS simulations, an optimization algorithm is used to predict IED equivalent charge mass ($M_{IED}$) and ($X_{IED}$, $Y_{IED}$, $Z_{IED}$) location. The results of IPS simulations are used as input for FPS simulations to compute blast loads on all human subjects. Blast loads are calculated on selected, injury sensitive, organs such as head and torso. The blast load simulations are then used to compute organ specific injury criteria which could be used for medical diagnostics. Pressure traces are computed at locations of virtual pressure sensor locations and results if predicted and measured pressure traces are used to evaluate accuracy of the method.

Figure 9:
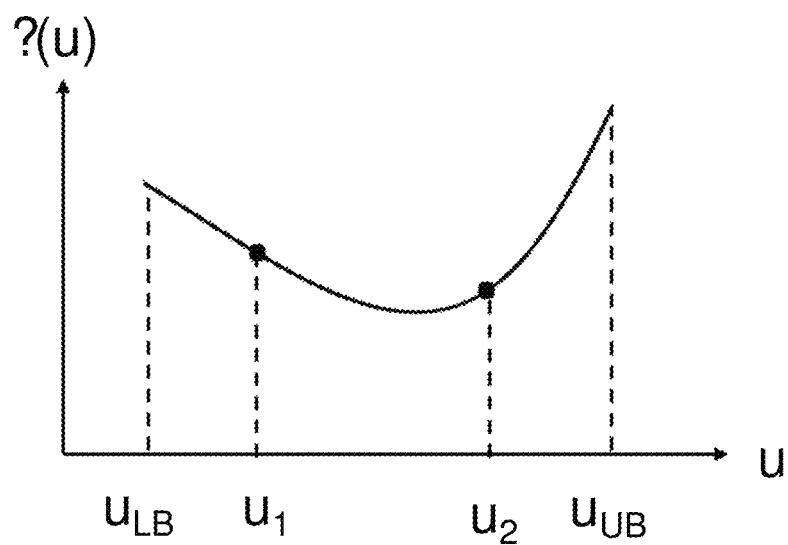
FIG. 9 includes a graph that shows optimization parameter estimation and error reduction.

FIG. 9 includes a graph showing the process of optimization parameter estimation and error reduction.

Figure 10:
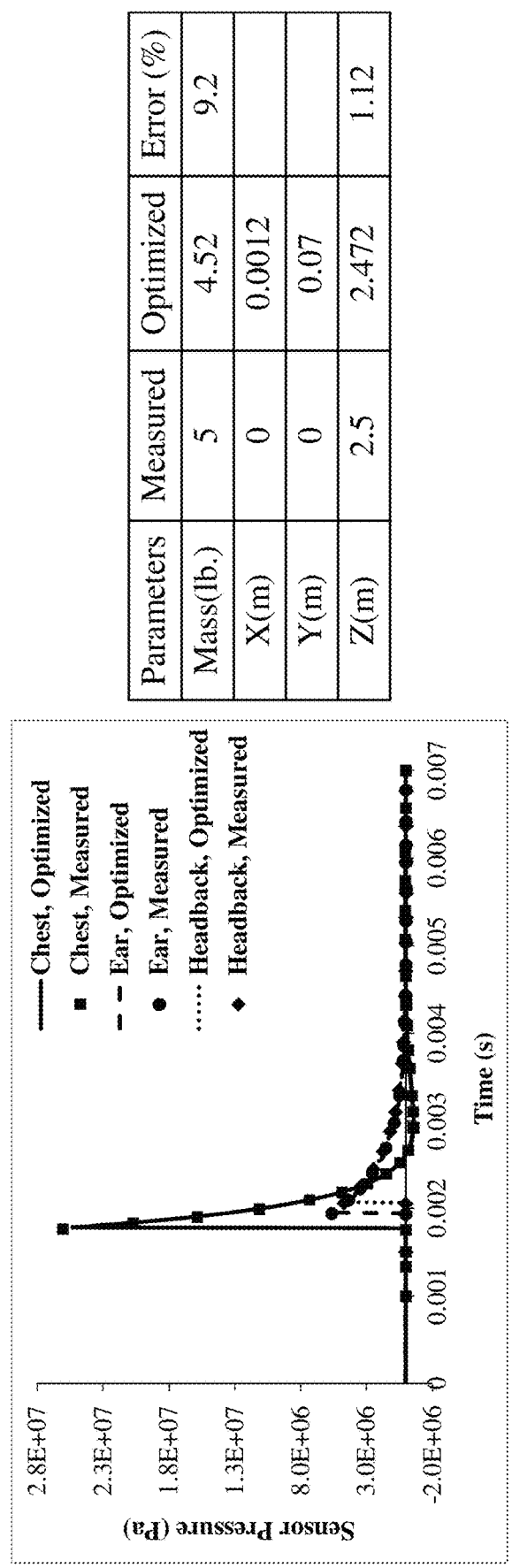
FIG. 10 includes data that provides a comparison between FPS predicted and IPS optimized pressure traces at three positions on the human body (chest, ear and back of the head).

The accuracy of the disclosed system and method to reconstruct an IED blast event depends on the quality of the pressure trace signals, number and spatial positions of the wearable sensors and knowledge of the positions and articulations of individual human subjects. To demonstrate the robustness and accuracy of the disclosed system and method, the FPS simulation results are obtained and used to calculate pressure traces at virtual sensors positioned on the human body chest, ear and back of the head. The results of the disclosed system and method in blast scene reconstruction and the accuracy of the predicted virtual pressure sensors are shown in FIG. 10. As shown, there is a very good agreement between "measured" pressure traces from FPS simulations and predicted pressure traces from IPS optimization simulations has been achieved.

In an example, the method used 5 lbs of C4 positioned in front of a human body above the ground, location of the explosion center is shown in FIG. 5. The IPS is used to obtain both explosive mass and explosive center location coordinates. In order to evaluate the sensitivity of wearable sensor locations on the human body, the method can use three groups of three wearable sensors located as follows: (1) forehead, right ear and back of the head; (2) chest sternum, right ear, back of the head, and (3) chest sternum, right arm, back side/spine, as shown in FIG. 5. FIG. 10 shows the comparison between FPS predicted and IPS optimized pressure traces at three positions on the human body (chest, ear and back of the head).

Figure 11:
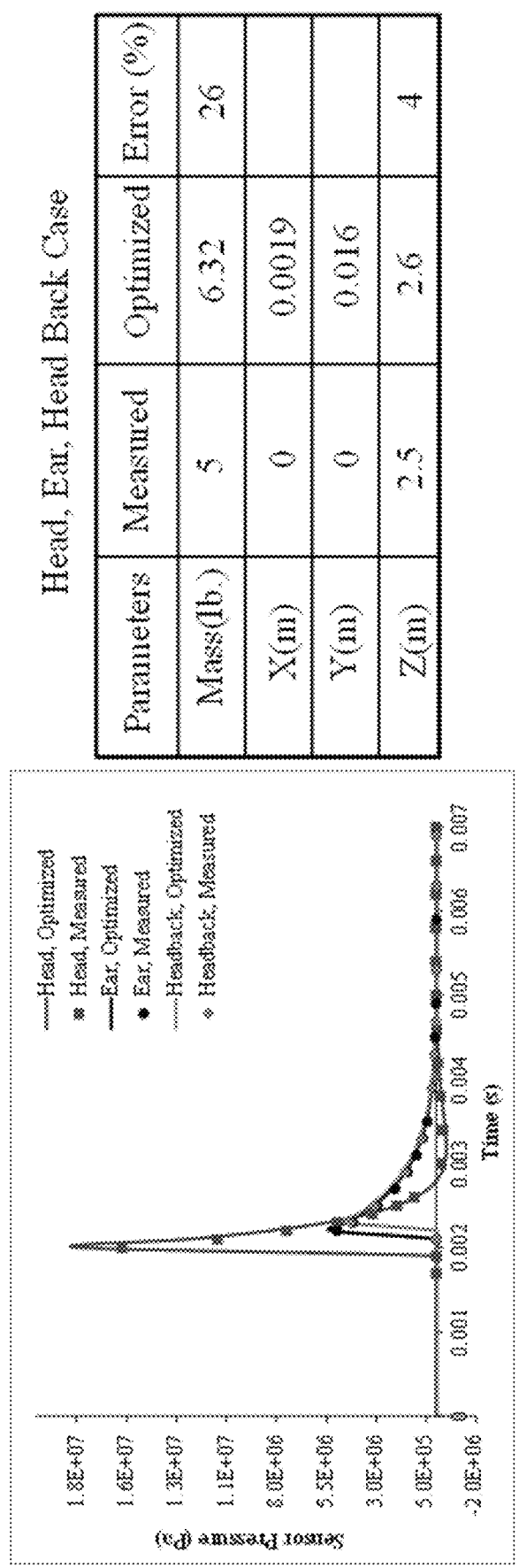
FIG. 11 includes data for a pressure time history comparison between recorded and simulated data for case (1) with head, ear and head back sensors.
Figure 12:
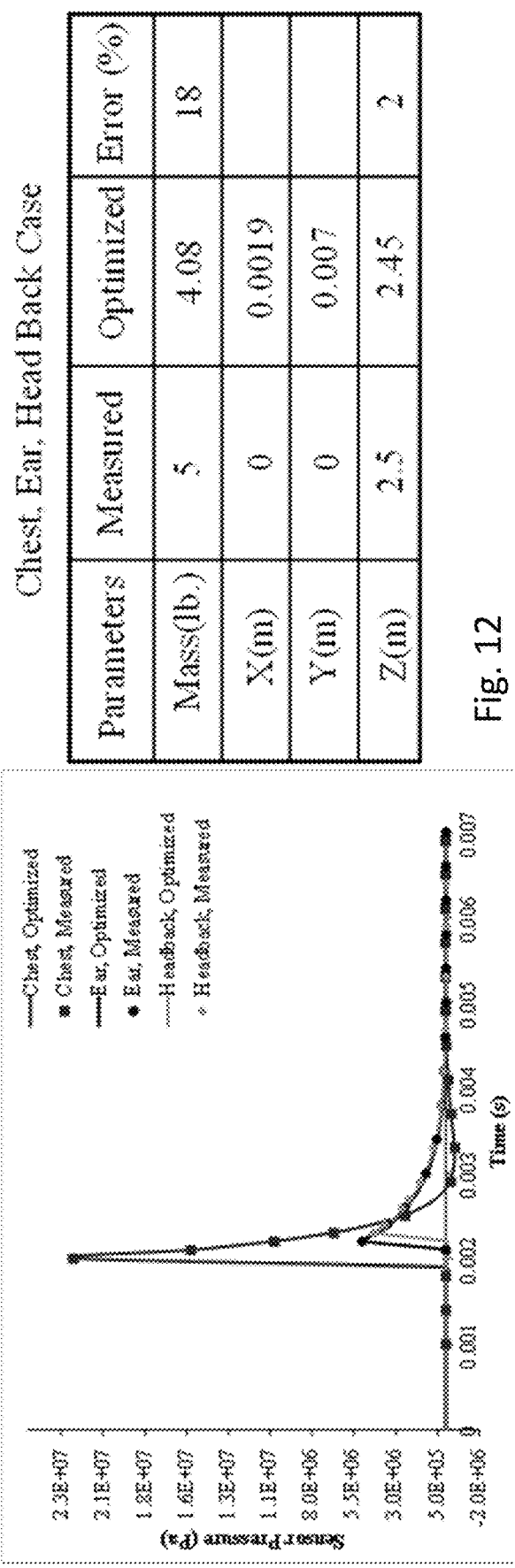
FIG. 12 includes data for a pressure time history comparison between measured and simulated data for case (2) with chest, ear and head back sensors.
Figure 13:
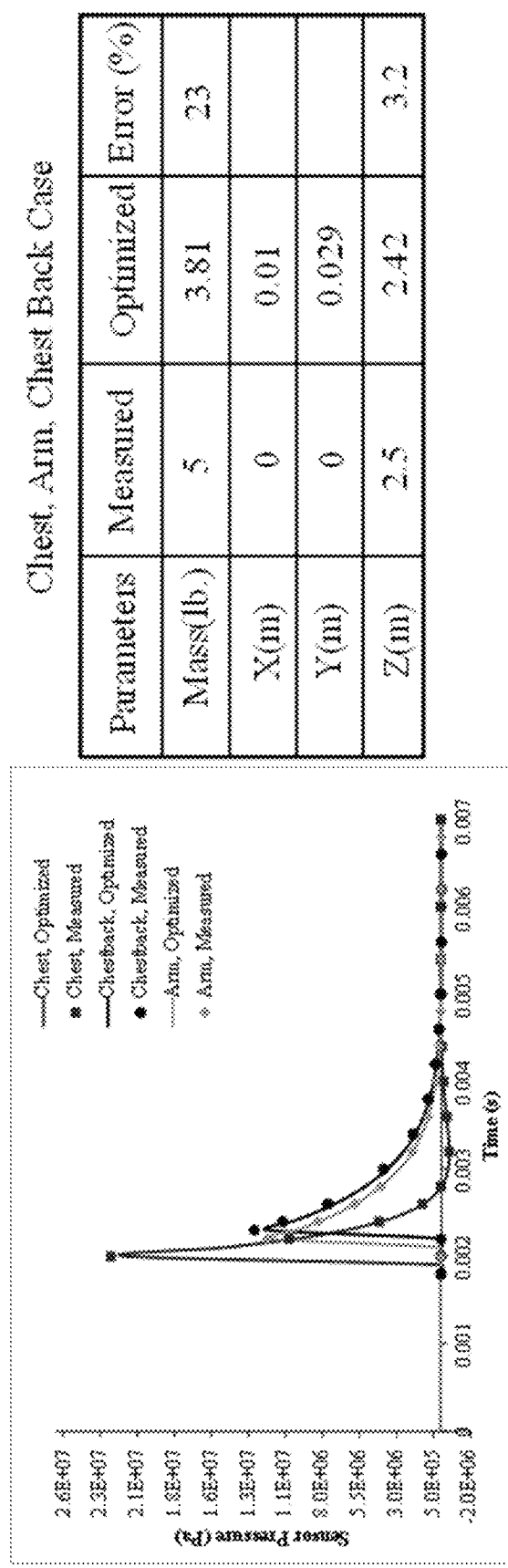
FIG. 13 includes data for a pressure time history comparison between measured and simulated data for case (3) with chest, arm and chest back sensors.

Then, the method uses the FPS to record blast pressure value at all sensors and then performed three inverse simulations to optimize the correct explosive mass and explosion location coordinates (x, y, z) with respect to the coordinate XYZ attached on the human body. In this coordinate system, the IED blast center is located at (x, y, z)=(0, 0, 2.5) m. Each inverse simulation used one set of pressure sensor data on the sensor configuration (1), (2) and (3) recited above. In the example, the shooting method is used to perform all inverse simulations. FIGS. 11 ((1) forehead, right ear and back of the head), 12 ((2) chest sternum, right ear, back of the head), and 13 ((3) chest sternum, right arm, back side/spine) show examples of pressure time history data obtained by the inverse problem solver comparing with the pressure data recorded earlier by forward simulation using the three sensor configures. The table inserts in FIGS. 11, 12, and 13 show the predicted explosion mass and center location coordinates (X, Y, Z). It is noted that the CoBi software obtains good solutions compared with measured data. Among the optimized parameters, the mass of the IED explosion has larger error than the location parameters. This may be caused by the extremely fast speed that the blast wave is passing over the sensor locations. The sensor pressure reaches the peak value almost at no time and this makes the slope of pressure curve extremely steep and in turn causes an error in optimized calculation. The accuracy can be improved by reducing the simulation time step, dt, at the cost of longer simulation time. However, the optimized explosive charge mass and distance are still quite accurate in all three cases.

The time step used in the inverse problem solver for the above three cases is $10^{-4}$ seconds for fast simulation, and 70 discrete data points used as "measured" data for the inverse solver. It is mentioned that the better accuracy could be achieved if reducing the time step for better capturing pressure sensor data. For the time step of $10^{-5}$ seconds and 700 discrete data points were used to perform the Chest, Ear and Head Back case (case 2) simulation. The comparison of pressure time history between optimized and forward simulation (used as a set point value) is shown in FIG. 10 left (graph) and the optimized parameters are listed in FIG. 10 right (table). The result shows the accuracy has been improved dramatically for a smaller time step in the compensation of long simulation time.

Figure 14:
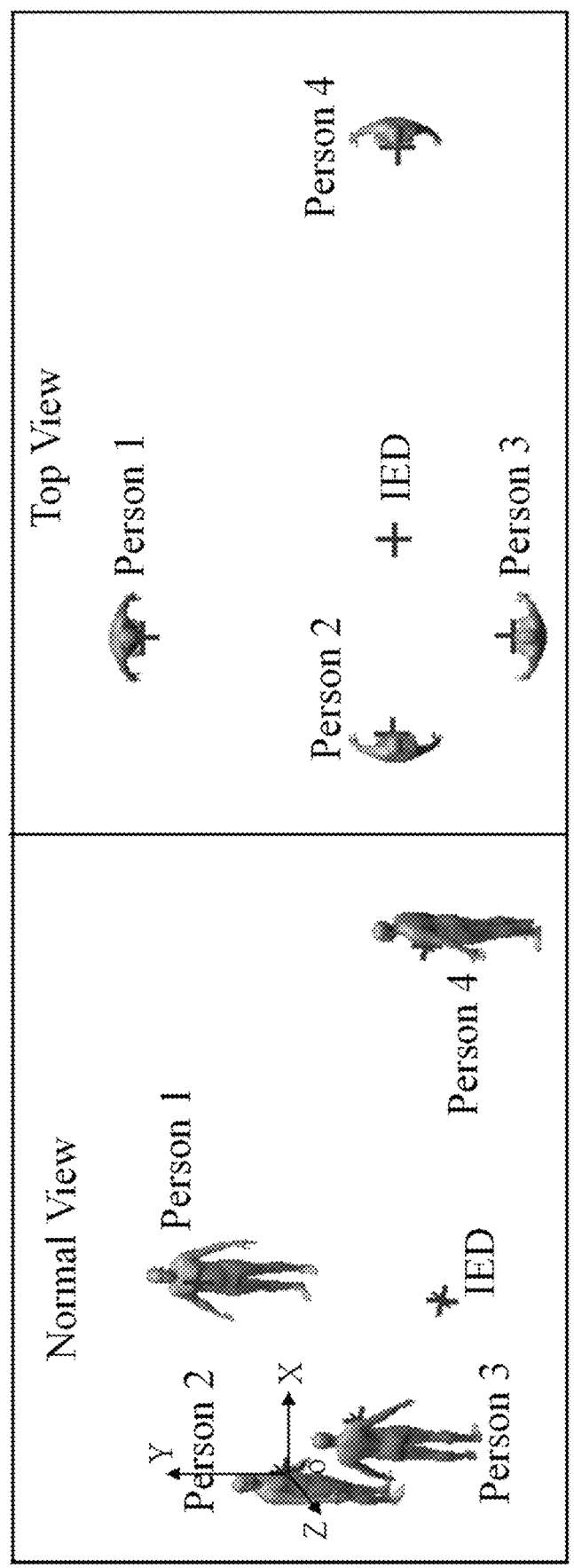
FIG. 14 includes a schematic representation of an IED blast scene involving four virtual human subjects having virtual pressure sensors on their chests.
Figure 15:
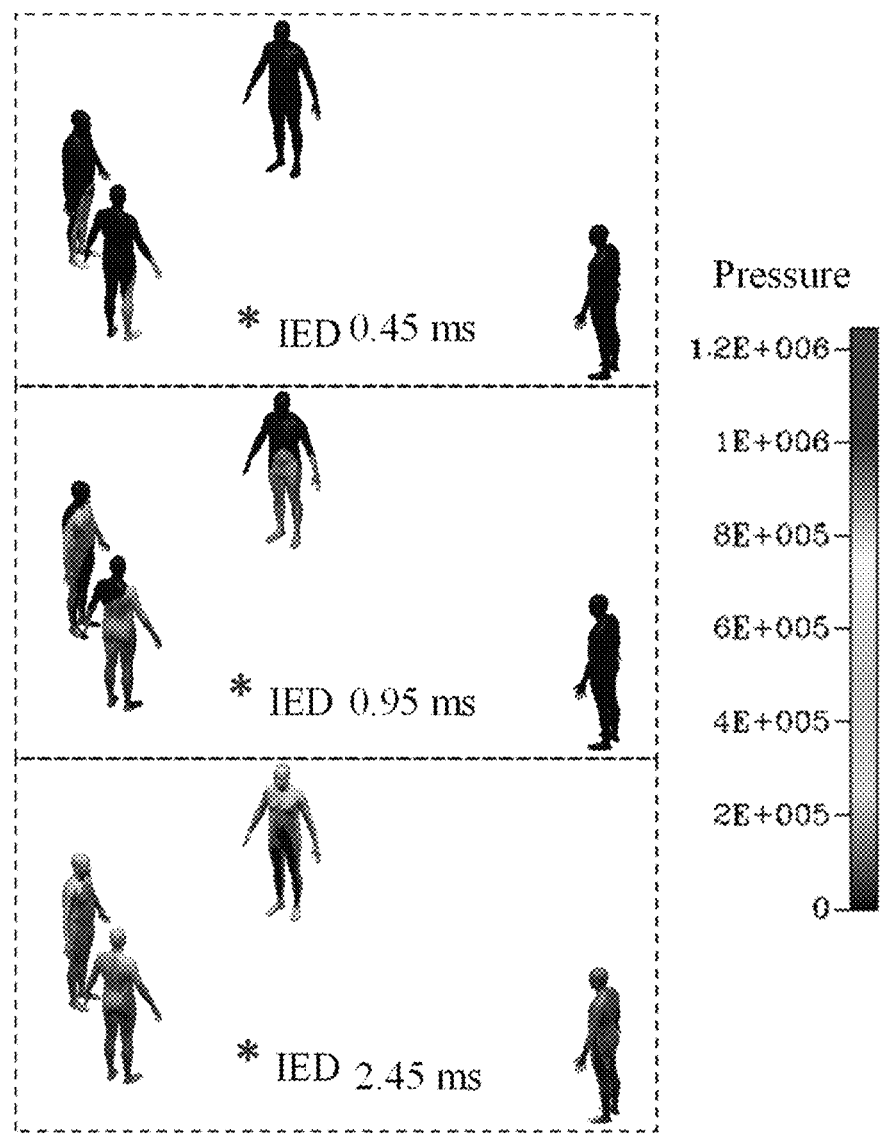
FIG. 15 shows the predicted blast loads on four human subjects at three time-instances (0.45 ms, 0.95 ms, and 2.45 ms) after the IED detonation.

In order to test the capability of the current optimization method, a study can simulate an IED blast on a group of people with unknown charge and unknown blast location. Each person is wearing a single pressure sensor on his chest to record blast pressure time history. A group of four people are arranged as in FIG. 14. First, the protocol performed a forward simulation to record blast pressure data. During the forward simulation, there was 5 lbs of C4 explosives and an explosion center at coordinates (x, y, z)=(2, −1, 0) m, as shown in FIG. 14. The pressure data obtained via forward simulation is used as an input to the inverse problem solver to predict the IED mass m and locations x, y and z. FIG. 15 shows the pressure field at selected times on each human body.

Based on the recorded pressure time history at four sensors, the IPS was performed to obtain the IED explosion charge mass m and explosion location (x, y, z). FIGS. 16A-D show pressure time history data obtained by optimized simulation comparing with those obtained in forward simulation. Table 2 lists the optimized IED explosion mass and location coordinates for minimizing the least squared error from all four persons' sensor data. We can see that, similar to the single person case, the largest error occurs at IED explosion charge mass which is the main reason for pressure to reach its peak value at the extremely short time. However, this accuracy can be improved by reducing a simulation time step. Overall, the optimized algorithm can obtain a good solution.

If the location of the IED and positions of individual persons are known the only optimization parameter is the IED mass. We run this case using the same pressure sensor data and, as expected, the IED mass is 4.82 lb with error of 3.6% which is much more accurate.

TABLE 2

Comparison of optimized IED parameters for all four persons - 70 data points

| Parameters | Measured | Optimized | Error (%) |
|---|---|---|---|
| IED mass | 5 | 3.93 | 21 |
| X | 2 | 2.005 | 0.25 |
| Y | −1 | −0.84 | 16 |
| Z | 0 | 0.0046 | |

Accordingly, the example shows the capability to reconstruct IED explosion events involving four different human subjects is demonstrated in FIG. 14. The IED is located on the ground, human subjects have different orientation relative to the IED and all four human subjects wear virtual pressure sensors on their chests. Predicted blast loads on four human subjects at three time-instances (0.45, 0.95, and 2.45 ms) after the IED detonation is shown in FIG. 15. Comparison between FPS predicted and IPS optimized pressure traces are collected at virtual locations (chest) for all four human subjects as shown in FIGS. 16A-D.

In one embodiment, a system and method are provided for automated reconstruction of an explosion blast event and blast wave loading on targets using pressure traces data from two or more pressure sensors. As such, the system and method can include: an explosion blast event of unknown strength and location; one or more targets exposed to such blast events; two or more pressure sensors mounted on such targets or nearby targets; methods of determining explosion blast strength and location; methods of determining blast wave loading on targets; and a system for sending sensor data to a computer or cloud system and computing and reporting blast strength, location and blast wave loading on targets. In some aspects, the targets are a human subject or plurality of human subjects. In some aspects, targets are structural objects including but not limited to robots, vehicles, equipment, buildings, and bridges. In some aspects, the pressure sensors are worn on a human body or mounted on targets or nearby targets. In some aspects, the pressure sensors are recording pressure as a function of time induced by the blast wave. In some aspects, the pressure traces of non-gated sensors are analyzed and time-aligned. In some aspects, other (optional) wearable sensor data are available such as accelerometers, microphones, carried mobile devices, and cell phones. In some aspects, the explosion blast strength and location are determined by analyzing sensor data using an IPS. In some aspects, the explosion blast strength, combined with a known explosive material, is used to compute the mass of the IED bomb or device. In some aspects, the explosion blast loading on targets are determined by using computed blast strength and location, and performing a forward problem simulation. In some aspects, targets are human subjects and blast loading on all organs and extremities (head, arm, legs) can be determined. In some aspects, blast loading data on specific organs are used to compute organ specific safety margins based on specified injury criteria, for example as to the brain, ear, eyes, lung, and intestines. In some aspects, blast loading data on specific organs are used to determine protective measures or treatments, for example post exposure resting periods, cumulative effects of repetitive exposures, pharmacological treatment of blast-induced traumatic brain injury, or amount of hearing protection needed. In some aspects, the predicted blast loading data can be used to determine the best/optimal (e.g. highest blast loading) location of a wearable sensor on or near a target.

In some embodiments, a system for reconstruction of an explosion blast loading on a subject can include at least two pressure sensors and a computing system configured to: receive sensor data from the at least two pressure sensors, the sensor data being generated in response to an explosion blast wave; compute an explosion location and explosive charge mass of an explosive that caused the explosion blast wave based on the sensor data; and compute explosion blast loading on a subject from the explosion location and explosive charge mass. In some aspects, the pressure sensors are configured as wearable pressure sensors. In some aspects, the pressure sensors are embedded in equipment configured to be worn by the one or more subjects. In some aspects, the pressure sensors are outfitted on a vehicle or equipment or drone or building. In some aspects, the computing of the explosion location and explosive charge mass includes processing the sensor data through an inverse problem solver (IPS); and/or the computing of the explosion blast loading on the subject includes simulating the explosion blast wave with a forward problem solver (FPS). In some aspects, the computing system is configured for performing a parameter optimization calculation when calculating the explosion location and explosive charge mass.

In some embodiments, the computing system can be configured for at least one of the following: processing anthropometric data of the subject; determining an arrangement of one or more body parts of the subject or one or more subjects with a scene generator computation; determining explosion blast loading on an organ of the subject; comparing the computed explosion blast loading of an organ of the subject with force related injury data for that organ; or determining whether or not the subject has an injury as a result of the computed explosion blast loading to at least one organ or body part of the subject.

In some embodiments, the computing system is configured to perform at least one of the following: reconstruct the explosion blast wave; create a computational model of the explosion blast wave; or reconstruct the explosion blast wave loading on one or more organs or body parts of the subject.

In some embodiments, the computing system is configured to perform at least one of the following: generating a topological layout of the explosion blast; identifying positions of individual subjects in the topological layout; selecting a reference subject for a coordinate system; determining relative orientation and postures for the individual subjects; generating a 3D anatomical model and creating virtual individual subjects for the individual subjects; positioning virtual pressure sensors on the virtual individual subjects; analyzing quality of measured pressure-time traces from the sensor data; and selecting a reference sensor based on trace signal quality.

In some embodiments, a method for reconstruction of an explosion blast loading on a subject can include: obtaining sensor data from at least two pressure sensors, the sensor data being generated in response to an explosion blast wave; computing an explosion location and explosive charge mass of an explosive that caused the explosion blast wave based on the sensor data; and computing explosion blast loading on a subject from the explosion location and explosive charge mass. In some aspects, the method can include calculating an injury to a specific organ of the subject based on predicted blast loads on the specific organ.

In some embodiments, the method can include: generating a topological layout of the explosion blast; identifying positions of individual subjects in the topological layout; selecting a reference subject for a coordinate system; determining relative orientation and postures for the individual subjects; generating a 3D anatomical model and creating virtual individual subjects for the individual subjects; positioning virtual pressure sensors on the virtual individual subjects; analyzing quality of measured pressure-time traces from the sensor data; and selecting a reference sensor based on trace signal quality.

In some embodiments, the method can include: generating a 3D anatomical geometry of the subject; computing the explosion location and explosive charge mass includes processing the sensor data through an inverse problem solver (IPS); and computing the explosion blast loading on the subject includes simulating the explosion blast wave with a forward problem solver (FPS).

In some embodiments, the method can include: collecting pressure sensor data from the at least two pressure sensors; identify location of each pressure sensor on one or more subjects in a blast zone of the explosion blast wave; analyzing the quality of sensor pressure-time traces of the pressure sensor data; selecting a reference sensor based on the signal quality and maximum pressure; determining whether or not the at least two pressure sensors are time gated; if not gated, then shifting the pressure-time traces in time relative to the reference sensor to become time gated; and inputting the time gated pressure-time traces into an inverse problem solver (IPS) calculation.

In some embodiments, the method can include obtaining anthropometric data for one or more subjects, and generating a 3D body anatomical model of the one or more subjects.

In some aspects, the method can include: identify subjects in a blast zone of the blast of the explosion blast wave having the at least two pressure sensors and subjects in the blast zone without a pressure sensor; obtaining a 3D body anatomical model of the one or more subjects; modulating the 3D body anatomical model for the one or more subjects by changing position and/or articulation; generating surface mesh data for the one or more subjects to have a 3D surface mesh for the one or more subjects; and determining locations of virtual pressure sensors on the 3D surface mesh for the one or more subjects.

In some embodiments, the method can include at least one of the following: processing anthropometric data of the subject; determining an arrangement of one or more body parts of the subject or one or more subjects with a scene generator computation; determining explosion blast loading on an organ of the subject; comparing the computed explosion blast loading of an organ of the subject with force related injury data for that organ; or determine whether or not the subject has an injury as a result of the computed explosion blast loading to at least one organ or body part of the subject.

In some embodiments, the method can include one or more of: determining whether or not the determined blast loading on the subject is above an injury threshold for one or more organs; correlating a blast loading on an organ of the subject with injury data for the organ; or determining a level of injury to an organ of the subject based on the determined blast loading.

In some embodiments, the method can include: determining protective measures to inhibit injury to an organ; determining a treatment to treat the injury to the organ; determining a post-exposure resting period for the subject; determining cumulative effects of repeated exposures to blast loading on an organ; determining a pharmacological treatment to treat the injury to the organ; determining protective equipment to inhibit injury to the organ; or determining modifications to protective equipment to inhibit injury to the organ.

In some embodiments, the method can include: implementing protective measures to inhibit injury to an organ of the subject; implementing a treatment to treat the injury to the organ; implementing a post-exposure resting period for the subject; implementing a protocol to inhibit cumulative effects of repeated exposures to blast loading on an organ; implementing a pharmacological treatment to treat the injury to the organ; implementing use of protective equipment to inhibit injury to the organ; or implementing modifications to protective equipment to inhibit injury to the organ.

In some embodiments, the methods can include calculating an injury to a specific organ of the subject based on predicted blast loads on the specific organ.

In some embodiments, the methods can include performing a parameter optimization calculation when calculating the explosion location and explosive charge mass.

Model-Based Calculations

In some embodiments, the systems and methods described herein can be used or modified for model-based calculations of blast loads on humans that are exposed to blast waves during military training and combat. The system can be configured to perform automated calculations of blast loads on humans exposed to blasts, whether from explosive materials or high-powered weapons. The systems and methods can use data from sensors that are strategically and/or arbitrarily placed in scenes for blast tests. The sensors can be wearable pressure sensors (e.g., wearable on a human or equipment) that provide data that can be used to calculate spatially distributed and time-resolved blast loads on the entire human body. For example, the blast loads can be calculated for injury sensitive organs, such as the face, head, neck, ears, eyes, nose, lungs, groin, and others. The system can use pressure traces data that can be collected from pressure sensors, where the sensors can be placed on or proximal with the blast causing device and on the humans within a blast wave zone.

In some embodiments, the system can be configured for integrated mobile sensor data collection, data processing, and storage in the system (e.g., on the computing system), the web, or cloud. The data can be accessed for real time or future analytics of human body exposure to multiple loads. The system can provide reports of blast loading reconstruction simulations [Tan et al. 2011] that can be used to correlate these with blast injury probability using experimentally collected "dose-response" data, [Gupta and Przekwas 2013].

In some embodiments, the system can utilize blast wave pressure trace data for specific weapons or explosive materials, referred to as the "weapon signature." That is, each type of weapon or each type of explosive material can be defined to have the weapon's signature. Data in the form of pressure versus time is collected from one or several sensors that are located in the proximity of the blast wave source (e.g., gun barrel exit, rifle muzzle break or mortar tube exit, etc.). These data are used to calibrate the disclosed inverse problem solver (IPS) to compute the "blast wave kernel" also known as the "shock wave kernel," which is a spatial volume (e.g., spherical, elliptical or other shapes) with specified pressure, temperature, density, energy, and momentum. The blast wave kernel provides initial conditions for fast "forward" simulations (e.g., FPS) of blast wave propagation and impact/loading on the blast-exposed humans and equipment at the sensors or at locations without sensors (e.g., any anatomical location or equipment location). The blast wave kernel can be used as described herein.

In some embodiments, the data from two or more pressure sensors are used to verify and validate the accuracy of the "forward" simulation step for predicting blast loads on a human body at locations having the pressure sensors. The data from multiple sensors located on one person, on multiple people, and/or on equipment can also be used to verify and validate the accuracy of the "forward" simulation step. As such, the at least two pressure sensors can be used and placed in various locations relative to the blast wave source.

As described herein, the system can use a reference x-y-z coordinate system (e.g. with z- in the vertical direction), which can be chosen to position the weapon or explosive charge (e.g., blast wave source) as well as to position people, both those who wear sensors and those who do not wear sensors. In some aspects, the system can use approximate human body anthropometric information in order to generate the human body 3D anatomic geometry. In some aspects, human geometry can be reconstructed from a picture or directly from an available body scan. In some aspects, the system is used to set up a blast event scene by positioning one human body or multiple human bodies in the x-y-z space and by adjusting each human body orientation and posture at the time of the blast exposure event. The sensor location (s) on the body may be known.

In one embodiment, human anthropometric data can be used to generate more accurate 3D body surface geometry. At least three anthropometric parameters are required (e.g., body height, weight, and gender) as inputs into the body anatomic geometry generator [Zhou et al. 2016]. Additional measurements, such as torso circumference, extremity lengths and others can be used as inputs to improve the resolution accuracy of the subject-specific anatomical geometry. If a body scan of a subject is available, the body scan can be used directly as input. Also, a scene generator, [Zhou et al. 2016], can be used to arrange one or more human body positions in x-y space, with specific orientations and articulations of individual human bodies. Human body models can be outfitted with clothing (e.g., military uniforms) and armor such as helmets, vests, and visors or other equipment (e.g., backpacks, holstered guns, gun slings, etc.).

The system can obtain a geometric representation of the weapon (e.g., mortar tube or recoilless rifle) and the position of the weapon relative to human bodies, such as the location and orientation of the recoilless rifle on the human shoulder. The system can also obtain the location of the blast wave kernel relative to the blast wave source, such as the weapon or blast wave source of the weapon (e.g. at the exit from the mortar tube). The blast wave kernel can be used as initial conditions for the simulation of the blast wave propagation, simulation of the blast wave impact on human bodies and equipment, and for calculation of blast loads on the body, body organs and equipment.

The blast wave kernel can be determined from the weapon signature experimental test, which collects pressure sensor data (e.g., pressure versus time) from sensors located at two or more spatial locations in the vicinity of the blast wave source of the weapon (e.g., rifle muzzle, mortar tube exit or back tube of the recoilless rifle). The sensor pressure traces can be "gated," such as with a common time instant following the weapon firing. In some aspects, the inverse problem solver (IPS) can be used to "gate" the sensors, such as described herein.

The pressure-time traces data from two or more sensors can be used to generate the weapon signature for each weapon, where the weapon signature can be used as inputs for the IPS simulations. The IPS simulations use a mathematical model of blast wave dynamics and parameter optimization algorithm, to compute the blast wave kernel. The blast wave kernel provides initial conditions for the fast "forward" problem solver (FPS) simulations of blast wave propagation and impact/loading on the blast-exposed humans and equipment.

The blast loads can be calculated on any human body and equipment that is exposed to the blast wave, whether wearing a pressure sensor or not. The FPS simulations can also be used to generate pressure traces by virtual sensors located on computational models of humans and at the physical pressure sensors. Also, the data of the physical pressure sensors can be used for calculations. Comparisons of pressure traces collected from physical sensors and virtual sensors can be used to evaluate the accuracy of the IPS reconstruction model.

In some embodiments, results of FPS simulations can be used to calculate space-time pressure loads on the entire human body or discrete portions thereof that are exposed to the blast wave. For example, the discrete portions can include selected body organs, such as head and torso, with vital organs that can be damaged by blast waves. The results can be used to calculate injury parameters, such as Head Injury Criteria (HIC) [Marjoux et al. 2008, Hutchinson 1998, Gupta and Przekwas 2013] or Chest Wall Velocity Predictor (CWVP) [Axelsson and Yelverton 1996, Przekwas 2008], which can be included in reports, and used to help in injury diagnostics and casualty care.

In some embodiments, the system and models can be used to collect or calculate blast load data from multiple and repeated blast exposures, such as during military training (e.g., from breaches and gunners), and the blast load data can be stored in digital form (e.g., as data or as a report) for medical analytics, diagnostics, and decision making to prevent neurological detriments. In some aspects, the blast load data can be used as the "dose" to correlate "dose-response" effects to medical outcomes, which can be included in the reports. The "response" can be in the form of cognitive, physiological or biological biomarkers, which can be obtained and analyzed as known in the arts. The system can then correlate the blast load data with the cognitive, physiological or biological biomarkers that result therefrom.

In some embodiments, the system and methods can be used for automated reconstruction of low-level blast exposure of humans (e.g., soldiers/warfighters) during training and/or combat scenarios. The training scenario can include a high-energy recoilless weapon, such as Carl-Gustav (CG) or a Shoulder Mounted Assault Weapon (SMAW) or a 50-caliber sniper rifle, where the back-blast and/or muzzle blast from the weapon(s) causes a low-level blast exposure on the operating soldiers. The low-level blast exposure is contrasted with the high-level blast exposure of an IED. The methodology allows for a comprehensive and localized blast overpressure evaluation and analysis across many training scenarios. The data and calculated results that are described herein can be saved for future use, and may be tagged to the humans for tracking the blast exposure of one or more humans over time. The cumulative effect of the blast loadings can then be analyzed and included in reports or for making improvements or preventing/treating injuries.

Figure 18:
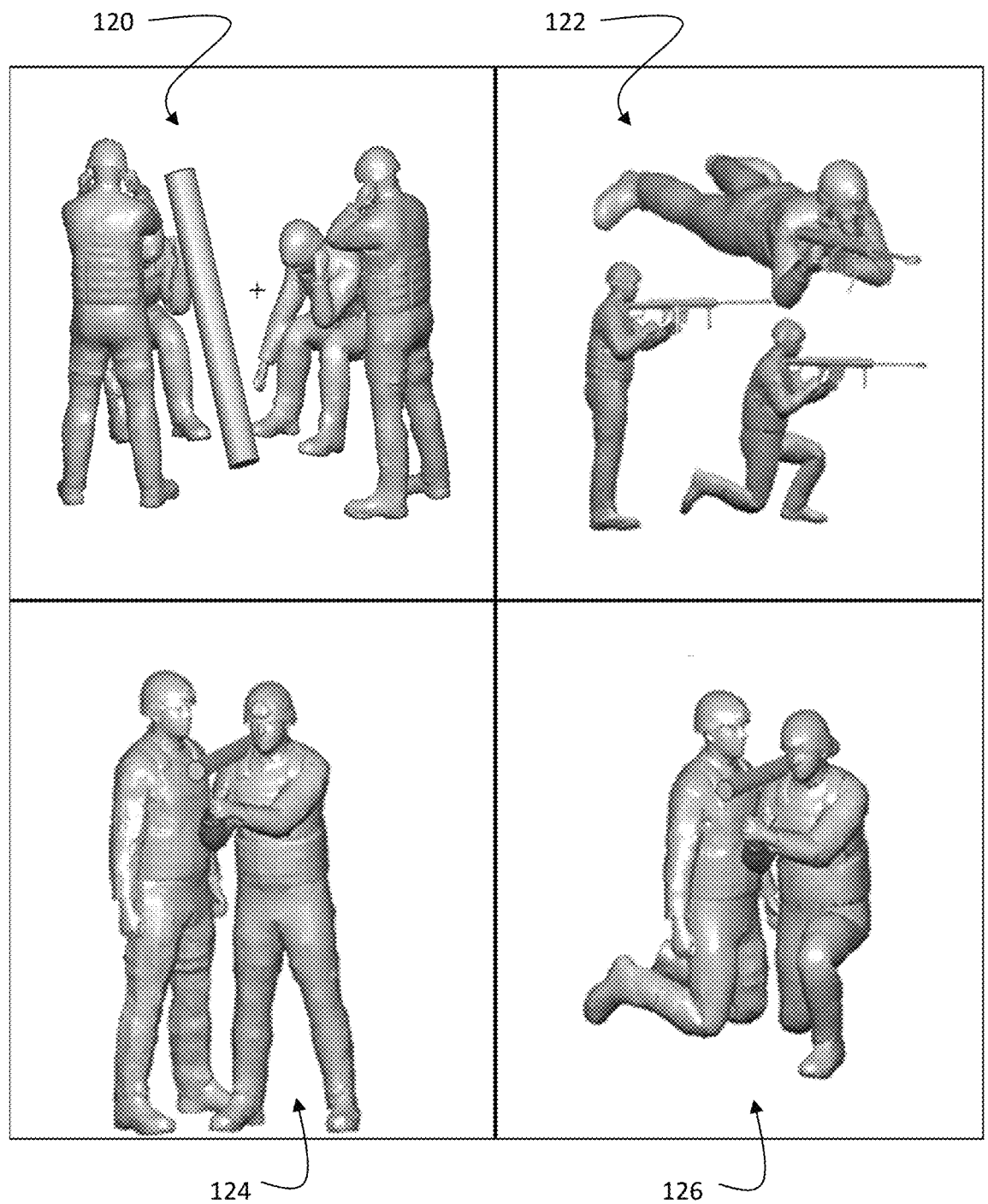
FIG. 18 illustrates a schematic representation of a model of a virtual training scenario and topological layout.

FIG. 18 shows some typical military training scenarios with one or multiple people being exposed to low-level blasts. The scenarios include a mortar crew 120 arrangement and anatomical positions, three different sniper 122 anatomical positions, a gunner team 124 arrangement and anatomical positions, and a kneeling gunner team 126 arrangement and anatomical positions. These arrangements and anatomical positions can be used in the calculations described herein. The arrangements can include a virtual training setup of the military crew during different training scenarios, with arrangement of body positions and the individual postures of the human bodies. Also, the arrangement can include the weapon, such as mortar, sniper rifle, and recoilless rifle. The arrangement can include the position, and orientation of the orifice (e.g., blast wave source) of the weapon from which the blast wave kernel is determined to originate from. Locations of blast sensors (e.g., pressure sensors) on individual human bodies (e.g. on the chest and helmet) can be used to reconstruct virtual pressure sensor traces from forward problem solver (FPS) simulations. The blast wave kernel is positioned at the weapon blast wave source for the gunners (e.g., mortar crew, artillery and snipers) training or at the location of the explosive charge for the breachers training. These scenarios can be used in the methods described herein.

In some embodiments, the system uses field data to generate the topological layout of the training scene and calculate the weapon signature for the blast. This data includes the anthropometric information and posture corresponding to different warfighter personnel, some of whom may have wearable pressure sensors, and pressure traces from on-field blast sensors. The weapon signature, calculated from the IPS, can predict the equivalent blast mass and charge. These data are subsequently used by the FPS for estimating the blast loads on the human body.

Figure 19:
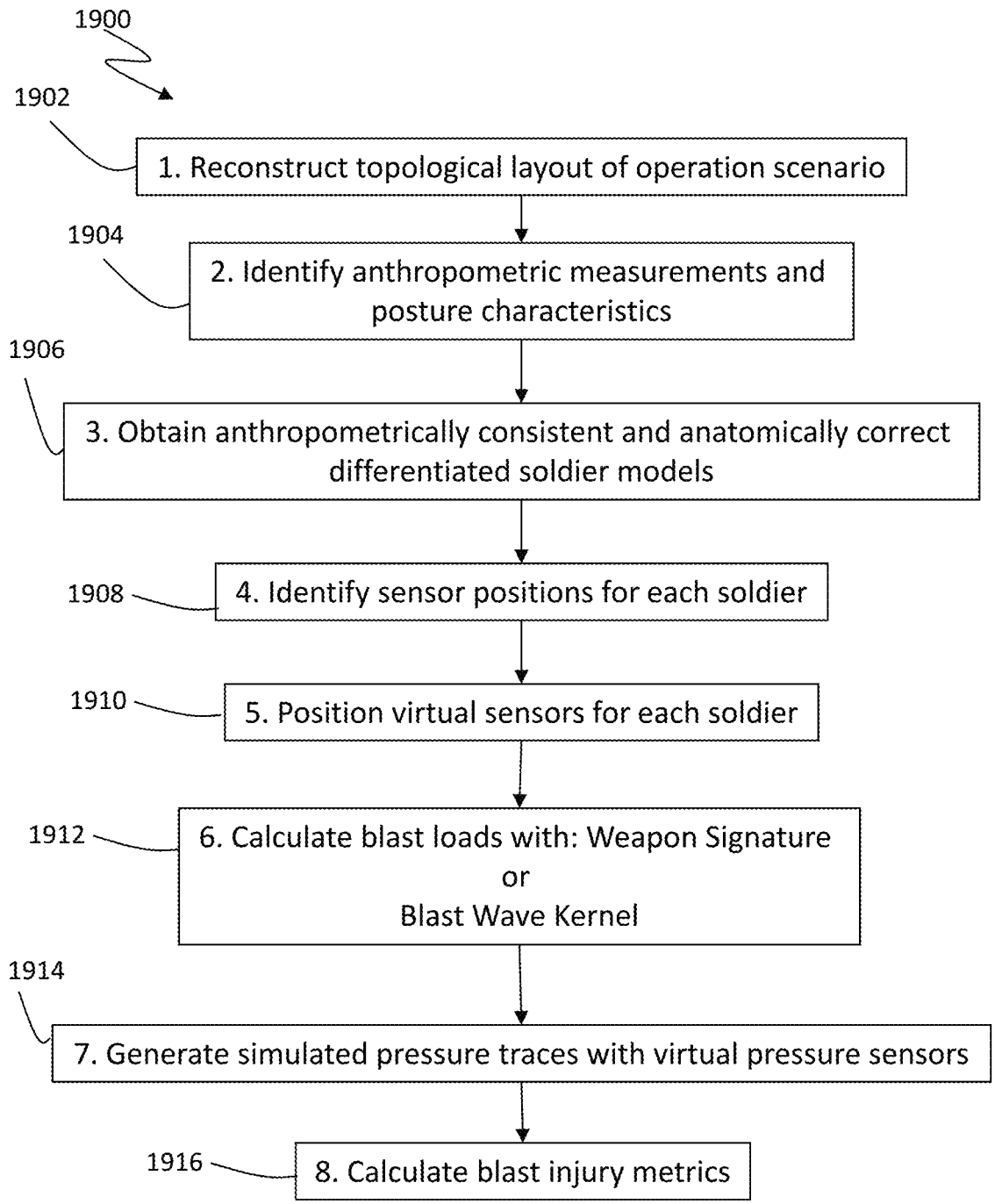
FIG. 19 includes a flowchart of a process for calculating blast wave loads on humans.

FIG. 19 includes a flowchart showing the main steps of the process 1900 of the system and method for the calculation of blast wave loads on human subjects during military training or combat operations. The method uses the weapon signature to position the blast wave kernel at the blast wave source. Step 1 can include reconstructing the topological layout of a training/combat operation scenario, such as from FIG. 18, which can show the individual soldier positions and articulations, and show the weapon position and orientation (block 1902). The weapon position and orientation can be used as a reference in order to identify the relative position of all of the human subjects. Step 2 can include identifying the anthropometric measurements and posturing characteristics of each individual soldier involved in the operation scenario (block 1904). Step 3 can include obtaining anthropometrically consistent and anatomically differentiated soldier models (block 1906), which can include using a high-resolution soldier model generator (e.g., human body models optionally equipped with clothing, protective armor, helmet and shoes). The position, orientation, and articulation of each individual soldier model can be made to accurately recreate the operation scenario. Step 4 can include identifying the wearable sensor positions for each soldier in the operation scenario (block 1908), which can include the height from the ground and position relative to the anthropometry and anatomy of that soldier. Step 5 can include positioning virtual pressure sensors on each individual soldier at locations corresponding to the real location of the physical body-worn sensors (block 1910). As such, the computer model of each soldier may be outfitted with the computer model of the pressure sensor at the locations that correspond with the real world. Step 6 can include calculating blast loads with Weapon Signature or Blast Wave Kernel (block 1912), which can be performed with obtaining the pre-determined weapon signature or equivalent blast wave kernel as described herein. The pre-determined weapon signature or equivalent blast wave kernel will correspond to the weapon in the training scene and be processed with the improved forward problem solver (FPS) to calculate the blast loads on each individual soldier, such as at different body parts. Step 7 can include generating the simulated pressure traces using virtual pressure sensors (block 1914). The accuracy of the methodology can be evaluated by comparing the measured pressure traces obtained from physical sensors against the virtual sensors. Step 8 can include calculating blast injury metrics (e.g., peak overpressure, positive impulse, negative impulse, organ specific injury criteria, injury diagnostics, etc.) using the predicted blast loads on the anatomical soldier model. The soldier model may be created and segmented into zones or regions, such as described herein.

Figure 23A:
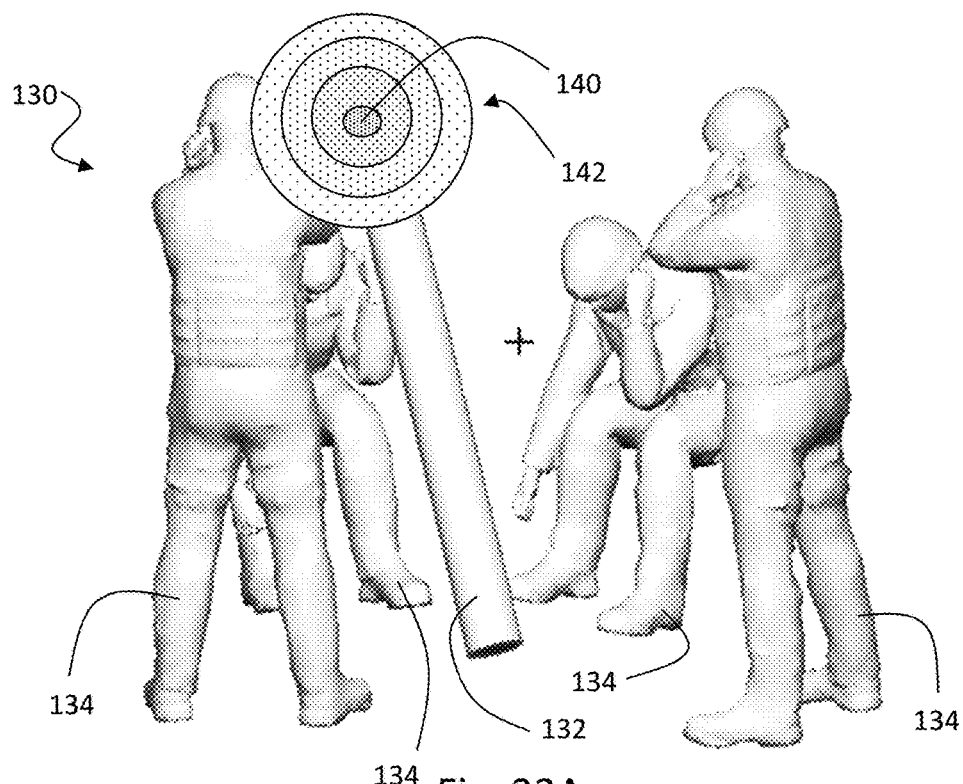
FIGS. 23A-23B include schematic diagrams of a virtual training scenario in a side view (FIG. 23A) and a top view (FIG. 23B).
Figure 23B:
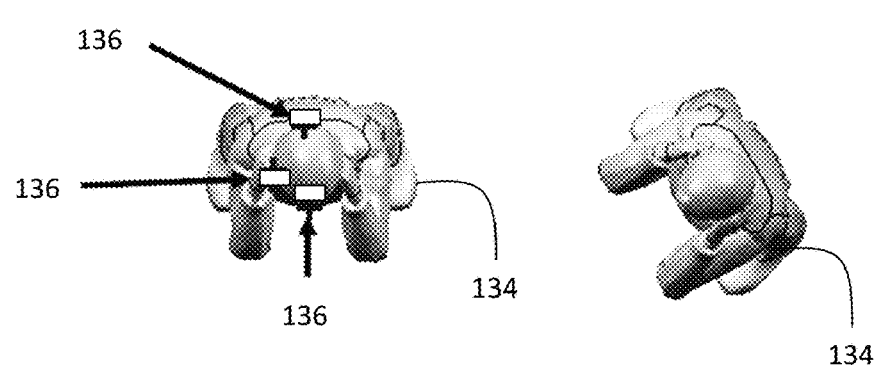
Figure 23B:
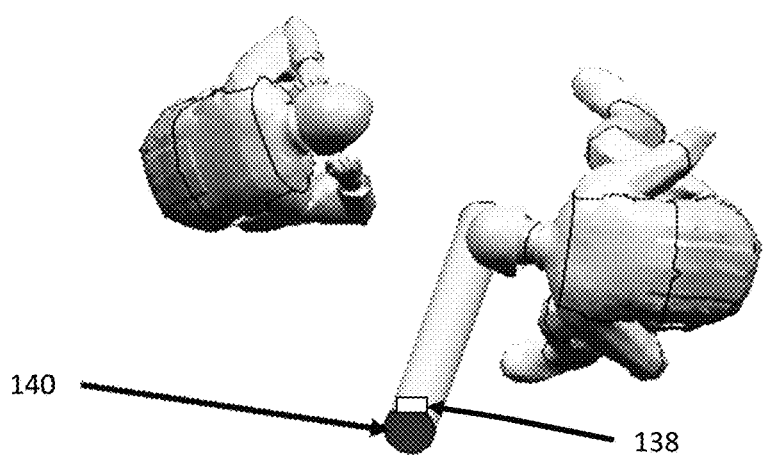
Figure 23C:
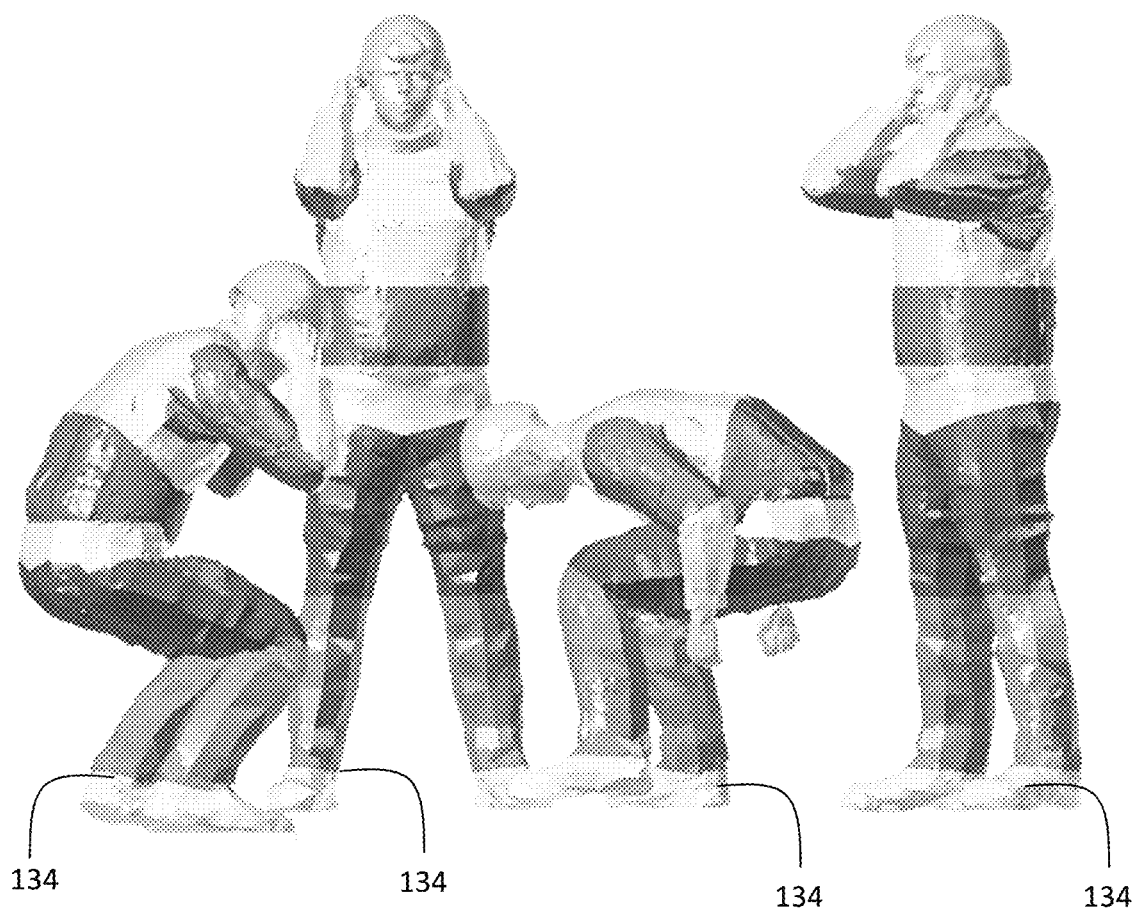
FIG. 23C includes a schematic diagram of a virtual training scenario with the virtual solder models being segmented.

The reconstructing of the computational model of the virtual training scene (e.g., operation scenario) can be performed as described herein. Previously, the different virtual soldier geometries, represented in the form of surface mesh (made of triangles or quads), can be used to generate a three-dimensional computational volume mesh, which adds un-necessary computational cost due to a large number of mesh nodes and elements that are required to represent the complex human geometry. Now, instead, the present technology can use layered volume meshes (similar to surface mesh but with thickness) to represent the intricate human body geometry and personal protective equipment (PPE), such as shown in FIGS. 23A-C). The methods can use meshing algorithms implemented in CoBi tools (e.g., CFDRC, for creating the computational mesh representations for all objects in a training scene. Absence of a background grid provides an additional computational advantage. These meshes are then integrated with the corresponding weapon geometries/meshes to reconstruct the computational models of the complete training virtual training scene or operation scenario.

Figure 20:
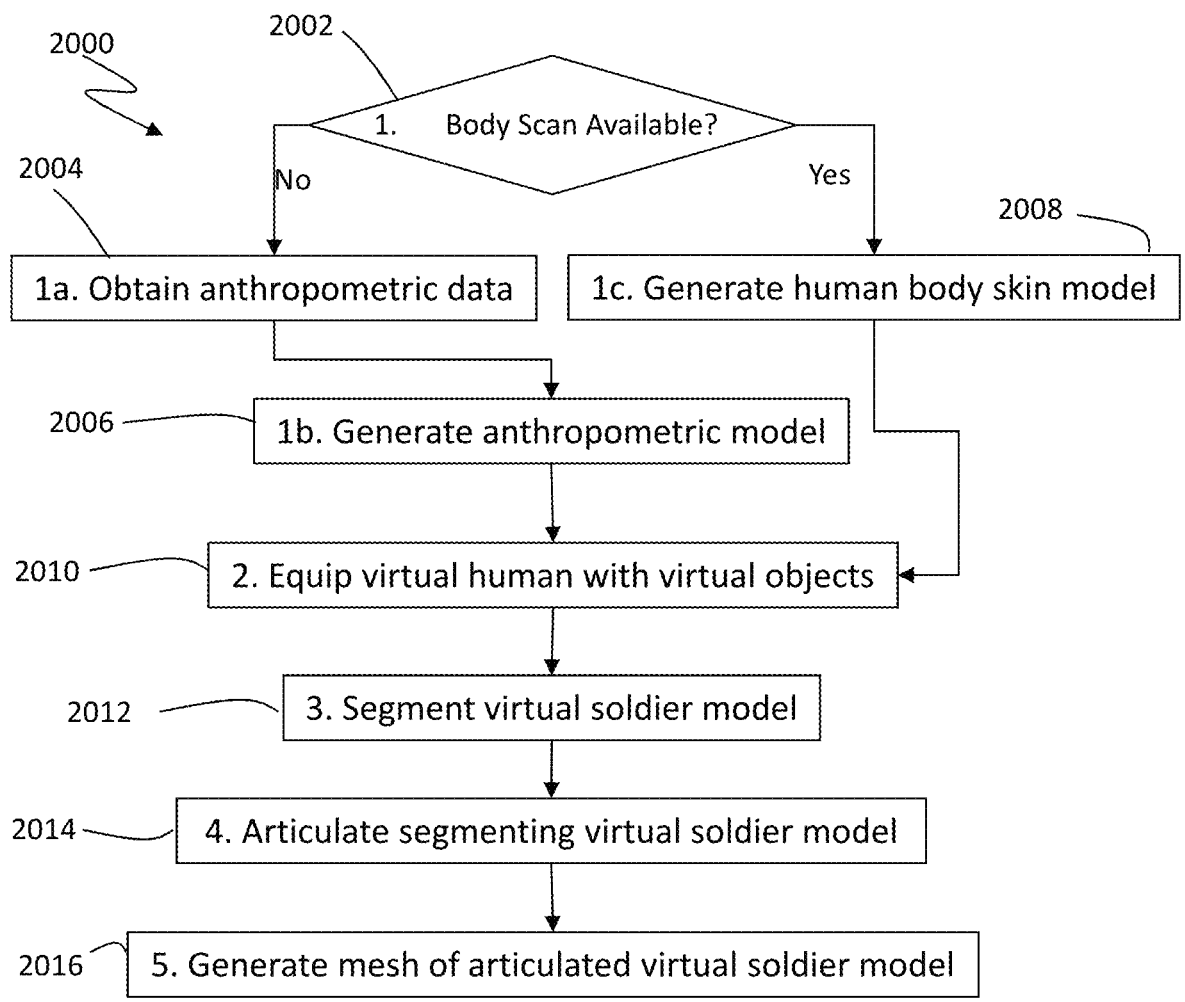
FIG. 20 includes a flowchart of a process for creating an anthropometrically consistent and anatomically segmented virtual soldier model.

FIG. 20 includes a flowchart showing the main steps of the process 2000 for creating an anthropometrically consistent and anatomically segmented "virtual soldier model". These virtual soldier models can be articulated as a physical human and used to create multiple complex training/combat scenarios. Basic anthropometric data are collected as inputs for generation of 3D human subject body models. If a body skin scan is available, it can be used directly to generate 3D body surface mesh. Otherwise an anthropometry-based 3D body generator is used to create the 3D body surface mesh.

The process can be performed as follows. Step 1 can include determining whether or not a body scan is available (block 2002). Sub-step 1a can include obtaining the anthropometric data (block 2004), such as by identifying and collecting the anthropometric characteristics (e.g., height, weight, gender, and any other measurements) for each individual soldier involved in the operations scenario. Sub-step 1b can include generating the 3D model of anthropometrically consistent human body geometry (block 2006), such as in STL format. The 3D model can be generated by the body model generator, such as described herein. In some instance, Sub-steps 1a and 1b are omitted when there is a body scan available, and instead, Sub-step 1c is performed. Sub-step 1c can include generating human body skin model (block 2008), such as by using surface rendering of the body scan to process the body-scan data and generate the 3D human body skin model in the STL format.

Step 2 can include equipping the virtual human body model (e.g., 3D anthropometric model) with objects, such as clothing, protective armor, helmet, and shoes to obtain the virtual soldier model (block 2010). Step 3 can include segmenting the virtual soldier model into discrete body regions (block 2012), which can be performed by using a human body segmentation generator that creates distinct segments of the human body. This can differentiate between different body portions that react to pressure trauma differently, such as the arm versus the head. Some differentiated body portions can include the head, upper thorax, lower thorax, groin, and appendages. Step 4 can include articulating the segmented virtual soldier model to recreate posture for each solder in accordance with the training scenario model (block 2014), such as shown in FIG. 18. Step 5 can include generating a surface mesh of the articulated virtual soldier in order to create a computational mesh for virtual training operation (block 2016). The surface mesh can be used for input for each soldier in the methods described herein.

As described, the generation of "virtual soldier models" can be performed as described herein. Reliable estimation of blast loads on different regions of the human body during a combat or training scenario requires an accurate representation of the human body position and posture with respect to the blast source. In some embodiments, the CFDRC human body model generator tools can be used to create models of individual soldiers/warfighters [Zhou et al. 2016]. The human body models can be prepared to correspond to the different personnel that are generated using the available anthropometric information, such as height, weight, chest width, head width, and others. If the body scan data is available, it will be used to generate the skin surface model (in STL format) using medical image processing and surface rendering. This virtual human body model is equipped with protective equipment such as helmet, armor, shoes, and clothing to create personalized virtual soldier models. The three-dimensional model will then be segmented into different body regions based on different anatomical joints using the CFDRC human body segmentation tool (see FIG. 23C). The segmented surface models are then articulated in the human body model generator to recreate the postural signature of the training scene. These individual soldier geometries are exported as 3D geometries in the STL format. This process is repeated for each team member depending on the training scenario.

The segmentation of the "virtual soldier models" can be performed as described herein. The full body skin surface models, equipped with clothing, armor, helmet and shoes, are segmented into different anatomical regions for a region-specific blast overpressure and injury criterion calculation (FIGS. 23A-C). This is achieved through the use of anatomically consistent joint locations. These joint locations are used to create joint planes with their normal oriented along the segments connecting the joint locations. The intersection loops created from the intersection of joint planes with the virtual soldier surface models are generated for smoother segmentation into different body regions. The bounding boxes created using the joint planes are then used to segment the single full body surface (in STL format) into different body regions based on the location of the different triangular patches comprising the STL model.

Figure 21:
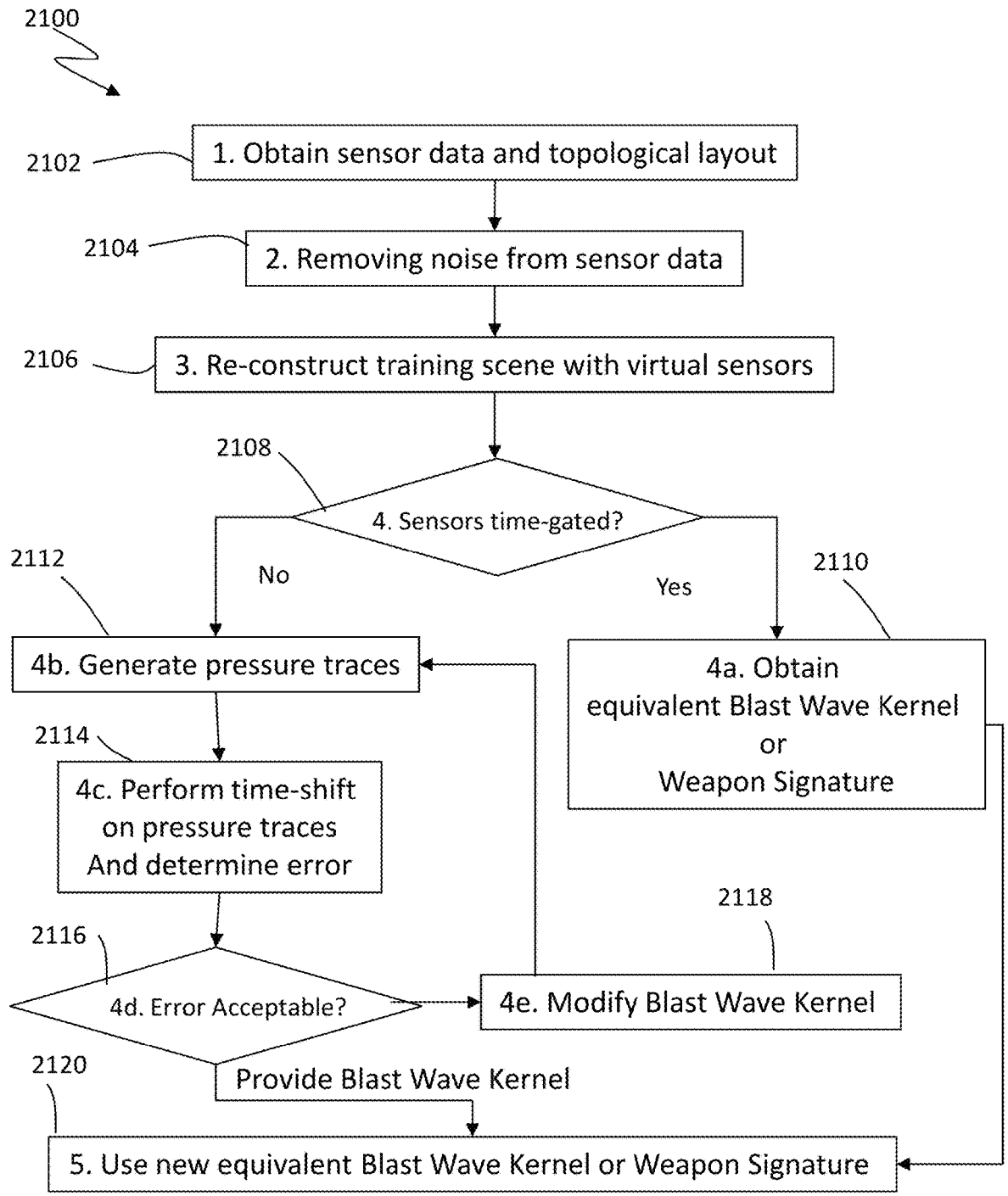
FIG. 21 includes a flowchart of a process for creating an equivalent Blast Wave Kernel or Weapon Signature.

FIG. 21 includes a flowchart showing the main steps of a process 2100 in the generation of the weapon signature in order to establish the parameters of the blast wave kernel (e.g., volume, pressure, temperature, energy and other physical properties) at the blast wave source. The pressure traces data from multiple pressure sensors positioned in the proximity of the blast source during the weapon signature generation test are used as inputs for the inverse problem solver (IPS) that is used to compute the blast wave kernel parameters. Similar experimental data, not used in IPS, can be used for the validation of the method. For non-time gated sensors, time shift relative to the reference sensor is performed. The process 2100 can include the following steps. Step 1 can include obtaining pressure trade data (e.g., pressure versus time) from sensors in training scenarios and obtaining topological layout of these sensors with respect to the position of the weapon and orientation and with respect to the ground (block 2102). The weapon's position and orientation can be used to improve blast analysis accuracy, and the position of the sensor with respect to the group allows for calculating blast waves that are reflected from the ground. Step 2 can include analyzing and processing the sensor data to remove any noise in order to provide improved sensor data (block 2104). Step 3 can include using the topological layout information in order to re-construct the training scene with virtual sensors placed at virtual locations that correspond with the physical location of the physical sensors (block 2106). Step 4 can include determining whether or not the sensors are time gated (block 2108): if yes, then Sub-step 4a is performed by using the time-gated pressure trace data as inputs into the IPS simulations in order to obtain the equivalent "Blast Wave Kernel" or "Weapon Signature" (block 2110); if no, then obtain time-gated pressure trace data (blocks 2112-2114). When the sensors are not time-gated, then Sub-Step 4b is performed by using the FPS to develop parametric cases (e.g., varying blast kernel characteristics) and generating the pressure traces at the different virtual free-field pressure sensors (block 2112). Step 4c can include performing a time-shift on the predicted pressure traces to match the arrival time of real sensor data (block 2114), and performing a quantitative comparison of the pressure trade data to calculate the error between predicted and real-life data. Step 4d can include determining whether or not the error is acceptable (block 2116). When the error acceptable, the protocol moves to block 2120; but, if the error is not acceptable, the protocol moves to block 2118. Step 4e can include modifying the Blast Wave Kernel characteristics based on the predicted pressure trace behavior at multiple virtual sensor locations (block 2118), and then Step 4b (block 2112) is performed again in the next iteration until the error is acceptable. Step 5, which can be performed after Step 4a or after 4d, can include using the new equivalent Blast Wave Kernel as the Weapons Signature for further simulations and parametric studies (block 2120).

The generation of the "Weapon signature" (i.e., equivalent Blast Wave Kernel) model can be performed using the Inverse Problem Solver (IPS). As described, the model invokes the IPS for the development of "Weapon Signature" models, which can also be described as equivalent Blast Wave Kernel models that reproduce similar blast loading profiles. Data in the form of pressure versus time is collected from one or several sensors located in the proximity of the blast wave source (e.g. gun barrel exit, rifle muzzle break or mortar tube exit). This sensor data is used in conjunction with the IPS to compute the "blast wave kernel", which is a spatial volume (e.g. spherical, elliptical or other shapes) with specified pressure, temperature, density, energy, and momentum. The blast wave kernel provides initial conditions for fast "forward" simulations of blast wave propagation and impact/loading on the blast-exposed humans and equipment. In another aspect, data from two or more pressure sensors can be used to verify and validate the accuracy of the "forward" simulation step for predicting blast loads on a human body at locations occupied by pressure sensors. The data from multiple sensors located on one person, on multiple people, and on equipment, in a training scenario, can be used to verify and validate the accuracy of the "forward" simulation step.

Figure 22:
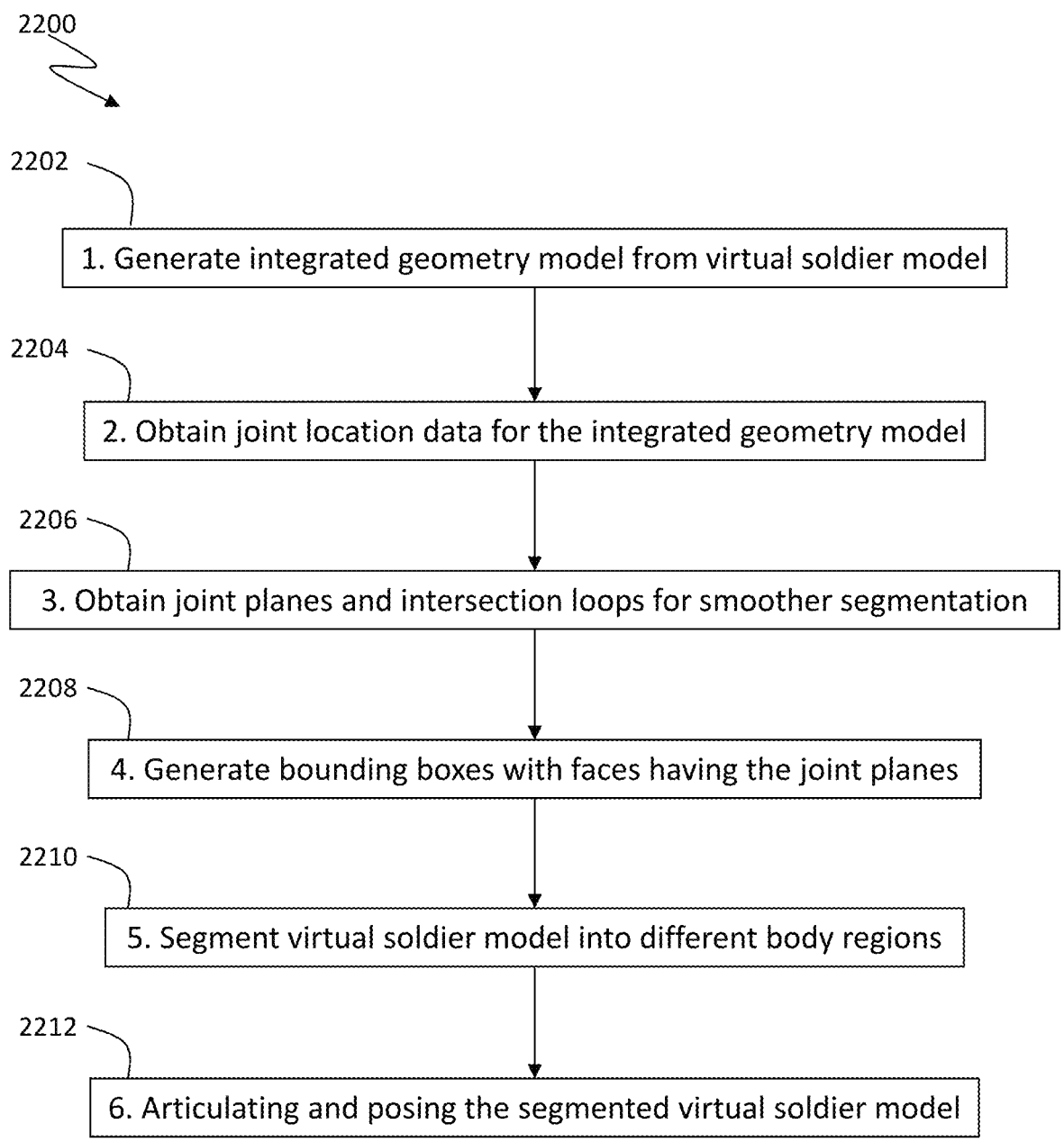
FIG. 22 includes a flowchart of a process for generating a virtual solder model with anatomical segmentation.

FIG. 22 includes a flowchart that shows the main steps involved in a process 2200 for the generation of the virtual soldier model with anatomical segmentation. The full body single surface model is segmented into different anatomical regions for high-resolution injury overpressure and injury analysis. Step 1 can include obtaining the virtual soldier model having the human body geometry (e.g., standing posture with arms in T-pose) that is equipped with clothing, protective armor, helmet, and shoes, and generating an integrated geometry model in STL format (block 2202). Step 2 can include identifying and collecting information on the anatomically consistent joint locations for the human body model (e.g., integrated geometry model) that is under consideration (step 2204). Step 3 can include using the joint locations to create joint planes with their normal oriented along the segments connecting the joint locations, and using the joint planes to generate intersection loops on the human body model (e.g., virtual soldier model) for smoother segmentation into different anatomical regions (block 2206), and then modifying the SLT information. Step 4 can include generating bounding boxes with faces having the joint planes (block 2208). Step 5 can include segmenting an input virtual soldier model into different body regions based on the location of triangular patches having the surface with respect to the bounding boxes (block 2210). Step 6 can include using the anatomically differentiated virtual soldier model in combination with the body model generator to articulate the model for accurate and realistic poses for training scenarios (block 2212).

In some embodiments, the IPS algorithm shown in FIG. 8 can be configured to use $u_1=m_{weapon}$; $u_2=x_{weapon}$; $u_3=y_{weapon}$; $u_4=z_{weapon}$ for the first guess for unknown parameters (block 801), then the protocol 800 can be performed. For the IPS simulations, an optimization algorithm is used to predict Weapon's blast kernel including mass ($M_{WEAPON}$) and ($X_{WEAPON}$, $Y_{WEAPON}$, $Z_{WEAPON}$) location. The results of IPS simulations are used as input for FPS simulations to compute blast loads on all human subjects. Blast loads are calculated on selected, injury sensitive, organs such as head and torso. The blast load simulations are then used to compute organ specific injury criteria which could be used for medical diagnostics. Pressure traces are computed at locations of virtual pressure sensor locations and the predicted results are compared against measured pressure traces to evaluate accuracy of the method.

FIGS. 23A-23C show schematic diagrams of the virtual soldier models illustrating an example weapon training scene 130 (e.g., mortar training crew) involving a high-energy weapon 132 and four human subjects 134 facing the blast/muzzle of the weapon 132. FIG. 23A is a side view and FIG. 23B is a top view of the scene. As shown in FIG. 23B, three virtual pressure sensors 136 are placed on each of the soldiers' forehead, ear and the back of the head to record virtual pressure traces using FPS simulation results. A blast source virtual pressure sensor 138 is also at the blast source at the muzzle of the weapon 132. The blast wave kernel 140 (e.g., also known as the effective weapon signature) of a blast 142 is placed at the muzzle of the weapon 132. FIG. 21C shows the segmented body regions.

Figure 24:
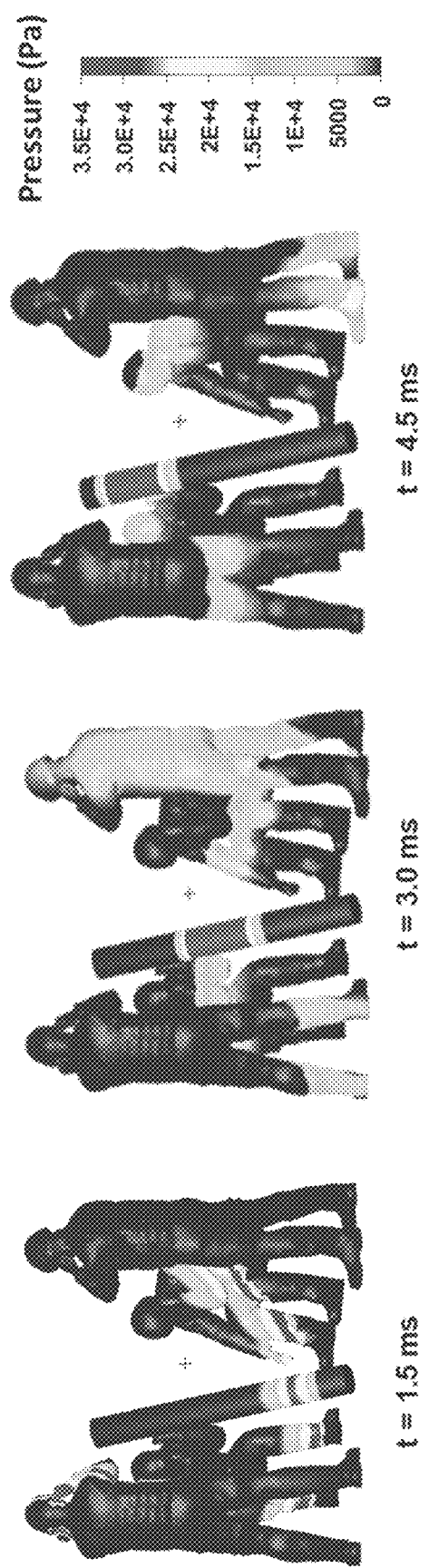
FIG. 24 includes results of a FPS simulation for an example operation of a military mortar firing scene and resulting blast wave propagation at 1.5 ms, 3 ms, and 4.5 ms.

FIG. 24 includes FPS simulation results for the example operation of military mortar firing scene and the resulting blast wave loading on the crew. Here, the FPS simulation predicted blast wave loads on a human body at three time-instances during blast wave propagation around the selected human body, such as at 1.5 ms, 3.0 ms, and 4.5 ms, where the pressure scale shows Pa.

Figure 25:
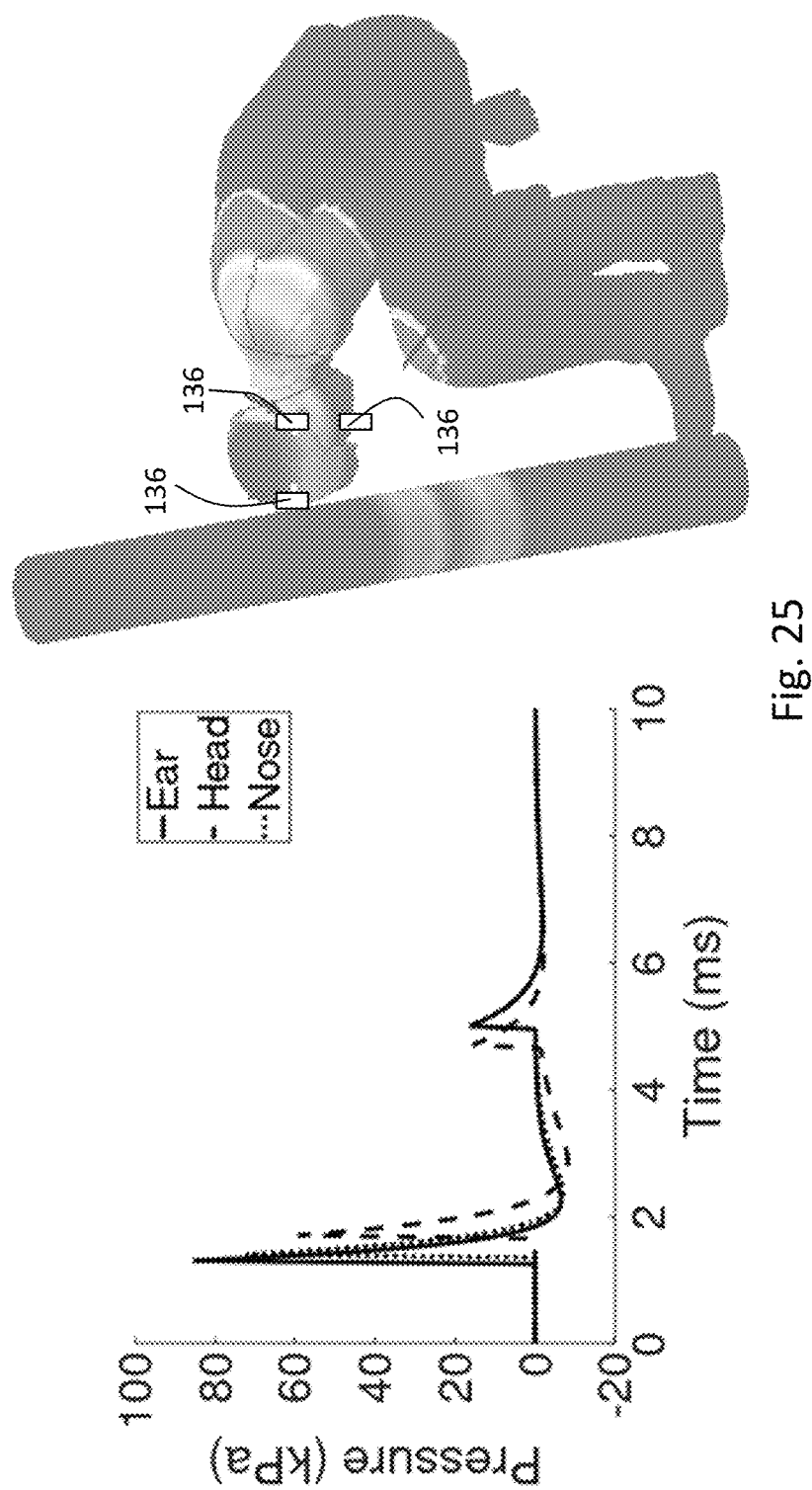
FIG. 25 includes a graph that shows calculated pressure traces at three locations using FPS simulations for the blast scene in the virtual training scenario of FIG. 23A.

FIG. 25 shows calculated pressure traces at three locations on the human head using FPS simulations for the blast scene shown in FIGS. 23A-23C. Three virtual pressure sensors 136 are placed on each of the soldiers' forehead, ear and the back of the head to record virtual pressure traces using FPS simulation results.

Figure 26:
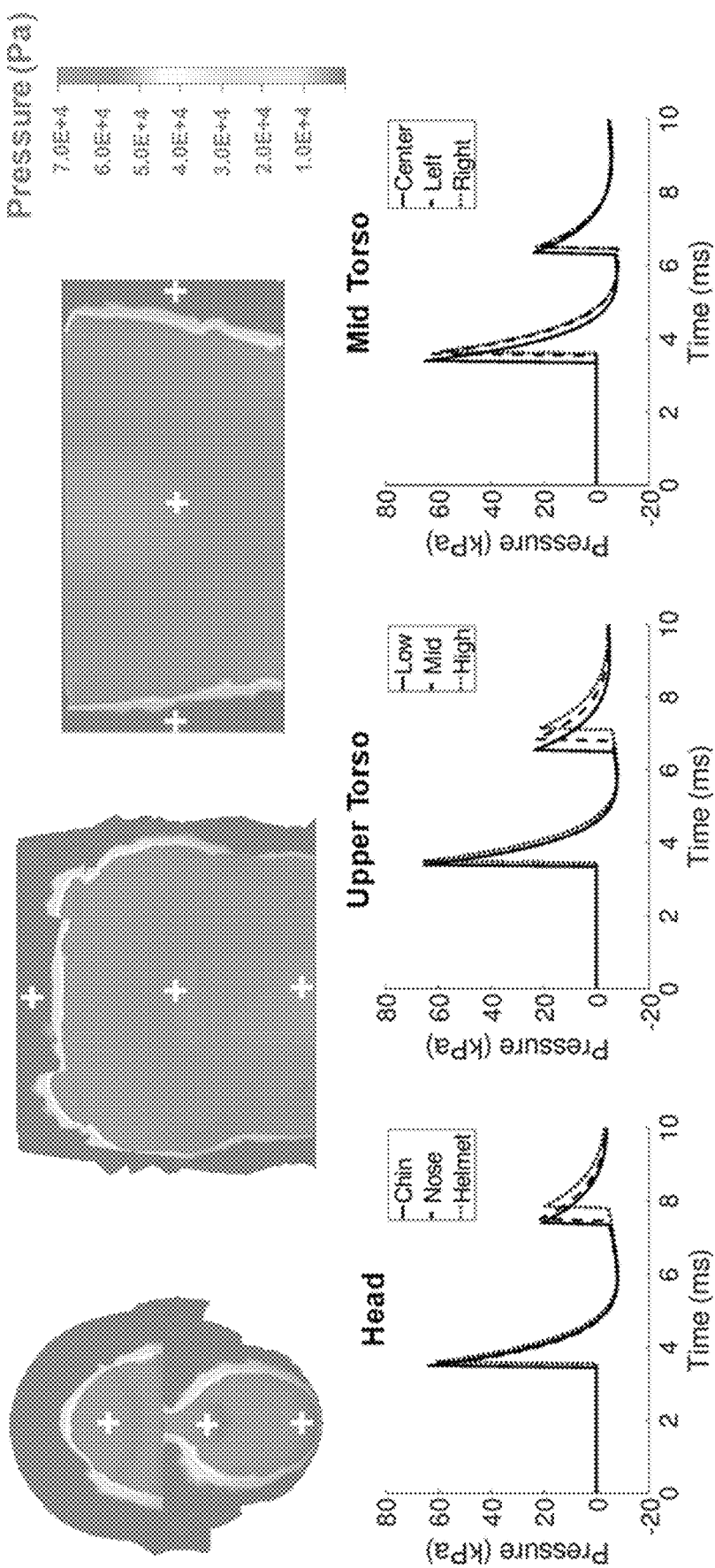
FIG. 26 includes graphs and associated anatomical schematics of blast overpressure loading on different anatomical regions of the virtual solder model.

FIG. 26 shows blast overpressure loading on different anatomical regions of the virtual soldier model, such as the head, upper torso, and mid torso. The central regions correspond with the higher pressures.

The following table provides information for each soldier, where each soldier can be tracked over time. The information identifies the body part and the relevant forces, pressures, and impulses.

mental data. The configuration can include pressure sensors at the head, wrists, and shoulder of the shooter. The blast wave kernel models generated from the sniper experiments and the FPS simulations have been used to compare model predicted and experimentally measured pressure traces for the recoilless rifle tests.

Figure 29:
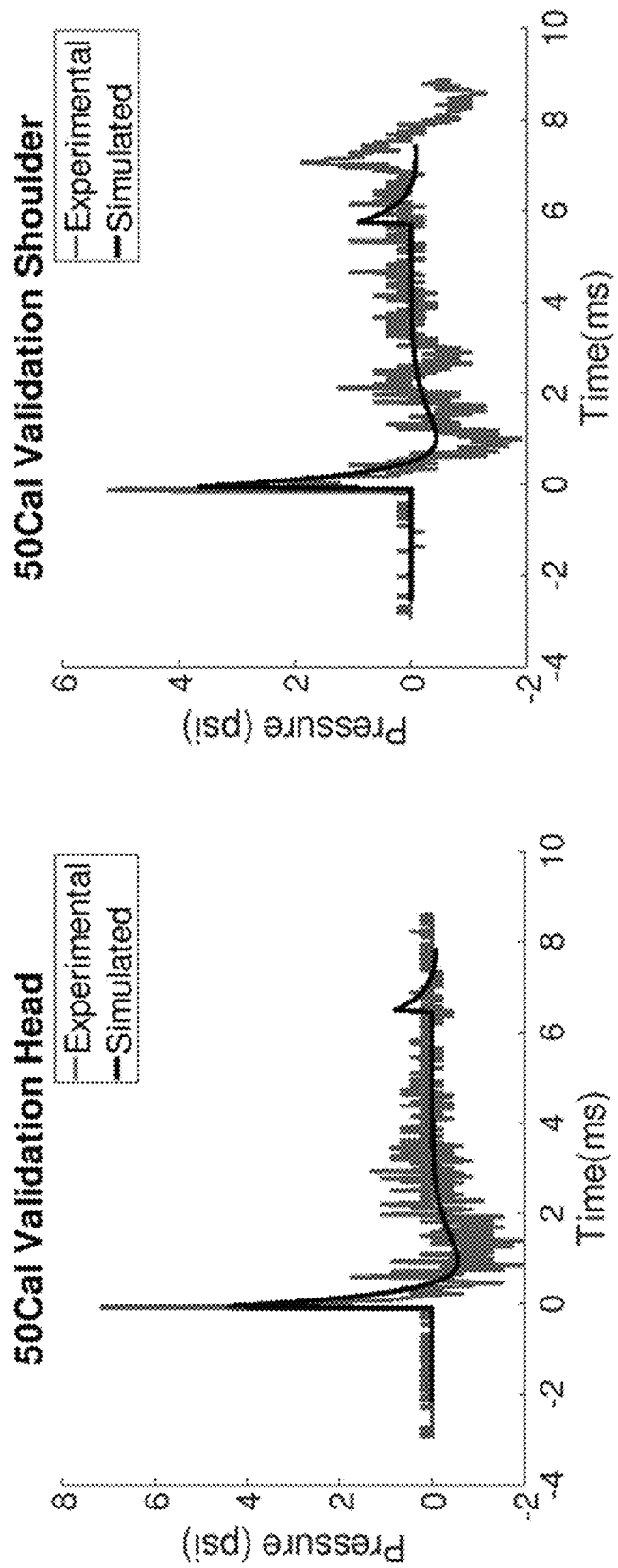
FIG. 29 includes graphs that show comparisons of experimental data versus simulated calculations for the head and shoulder of a virtual solder model of a sniper.

FIG. 29 includes graphs that show the comparison of pressure traces from virtual sensors placed at the head, shoulder, and wrist locations of the virtual sniper model to that of the real physical sensors.

Accordingly, in order to simulate the blast loads on human subjects during a combat/training scenario, the system can use three simulation algorithms: 1) Generation of 3D anatomical geometry of human subjects and the setting up of Weapon training scene (see FIGS. 20 and 22; and 2) Developing the Weapon Signature model using the inverse problem solver (IPS) (See FIGS. 8 and 21; and 3) Using the Forward Problem Solver (FPS) for calculating weapon-induced blast loads on different human subjects and different regions of a human body (demonstrated in FIGS. 23A-C to 26).

Information obtained from the protocols shown in FIGS. 19-22 can be used in any of the methods of FIGS. 2-4, and

| Soldier Label | Body Part | Peak Force (N) | Peak Pressure (psi) | Peak Impulse (Pa · s) | Peak Positive Impulse (Pa · s) | Peak Negative Impulse (Pa · s) |
|---|---|---|---|---|---|---|
| Soldier One | Whole-Body | 279.559 | 108.87 | 116.839 | 138.677 | −11.365 |
| Soldier One | Head | 56.209 | 55.73 | 116.839 | 138.677 | −21.128 |
| Soldier One | Mid-Torso | 7.393 | 7.55 | 75.131 | 97.878 | −19.749 |
| Soldier One | Upper-Torso | 184.32 | 45.01 | 104.751 | 126.459 | −19.552 |
| Soldier Two | Whole-Body | 470.863 | 71.64 | 95.999 | 118.18 | −13.752 |
| Soldier Two | Head | 96.705 | 87.1 | 87.048 | 103.261 | −13.752 |
| Soldier Two | Mid-Torso | 28.766 | 9.82 | 75.512 | 98.314 | −20.665 |
| Soldier Two | Upper-Torso | 186.523 | 60.29 | 88.42 | 107.43 | −16.764 |
| Soldier Three | Whole-Body | 101.276 | 14.42 | 31.605 | 52.309 | −15.07 |
| Soldier Three | Head | 9.649 | 9.82 | 22.602 | 42.466 | −15.861 |
| Soldier Three | Mid-Torso | 93.345 | 45.02 | 21.878 | 43.072 | −15.442 |
| Soldier Three | Upper-Torso | 20.934 | 7.54 | 22.969 | 43.417 | −15.07 |
| Soldier Four | Whole-Body | 82.696 | 12.48 | 24.624 | 47.472 | −7.104 |
| Soldier Four | Head | 9.101 | 7.23 | 23.038 | 35.393 | −9.14 |
| Soldier Four | Mid-Torso | 102.375 | 108.87 | 24.545 | 36.441 | −7.44 |
| Soldier Four | Upper-Torso | 10.849 | 9.47 | 24.624 | 36.282 | −7.104 |

Figure 27:
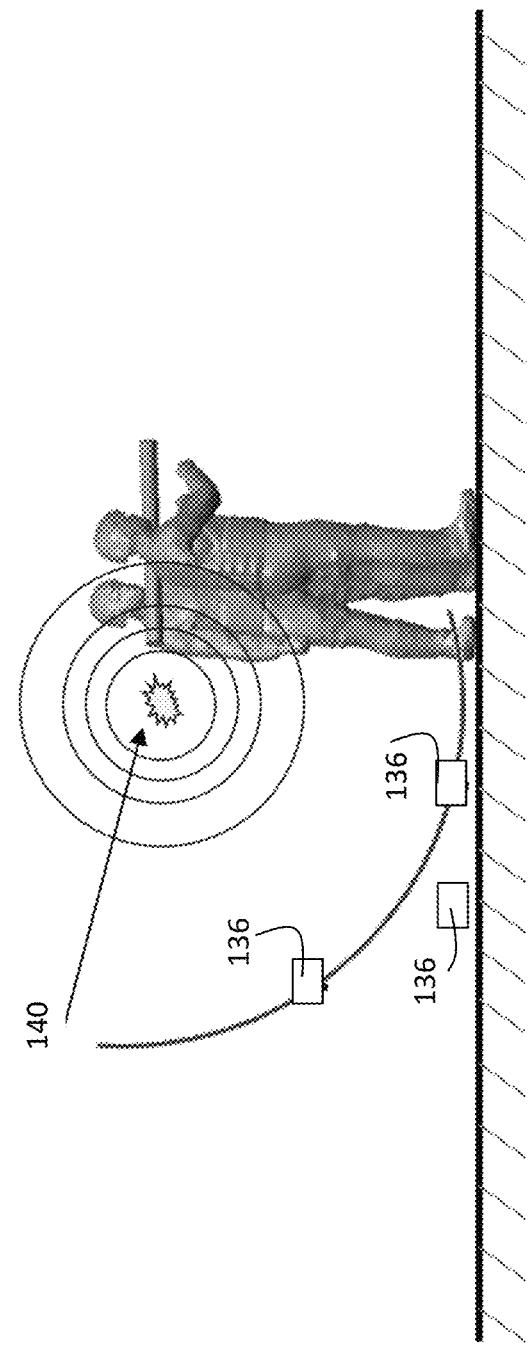
FIG. 27 include a schematic diagram of a training scenario for generation of a Weapon Signature (e.g., equivalent blast wave kernel).

FIG. 27 includes a schematic of training setup used for the generation of "weapon signature" for Carl Gustaf using published data [Wiri 2016, Win et al., 2017]. The "blast wave kernel" model generated from the gunner experiments and the FPS simulations have been used to compare model predicted and experimentally measured pressure traces for the recoilless rifle tests (FIG. 26). Virtual sensors 136 are included in the scene.

Figure 28A:
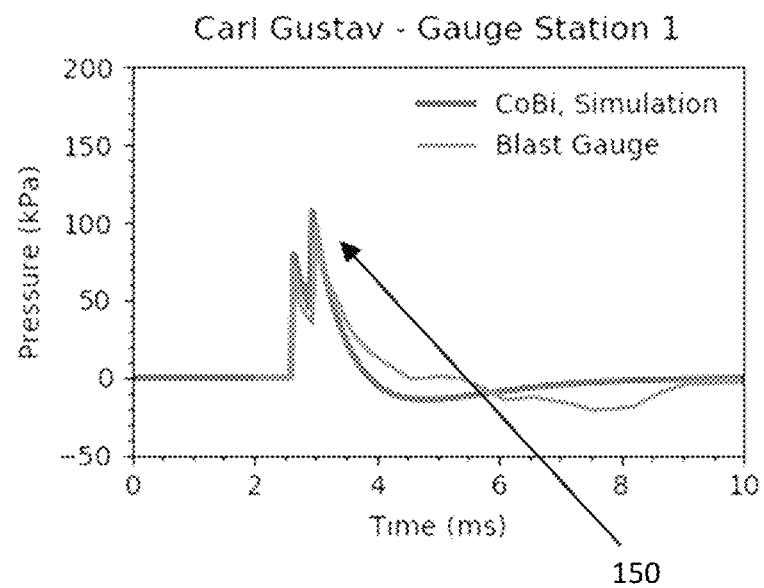
FIGS. 28A-28C include graphs that show a comparison of pressure traces at three different virtual pressure sensors compared to recorded blast gage data (e.g., pressure sensor data).
Figure 28B:
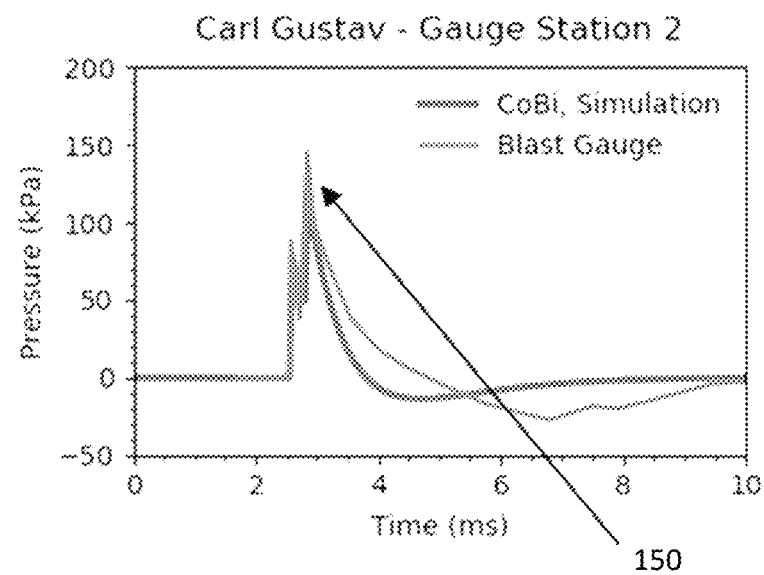
Figure 28C:
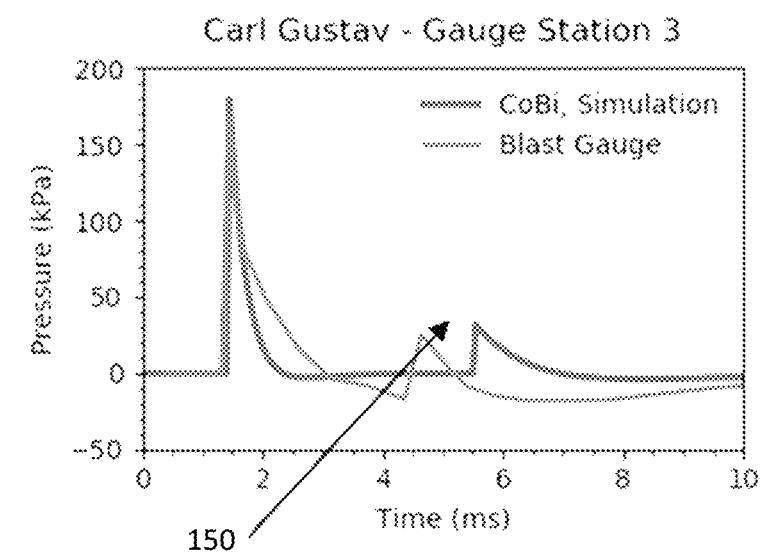

FIGS. 28A-28C include the graphs that show the comparison of pressure traces at the three different virtual pressure sensors added to the soldiers in the training scenario in FIG. 27. The pressure traces at different sensor locations demonstrate that the system can be used to generate accurate weapon signatures. Reliable pressure traces were observed at the different pressure sensors due to the implementation of ground reflection capabilities into the improved FPS. Generally, the blast gauge data (lighter, thinner) (e.g., pressure versus time) has more variability and inconsistencies than the smoother simulation data (darker, thicker). These figures show the secondary overpressure peaks 150 due to the addition of ground reflection of the blast wave.

A sniper or other shooter training setup can be used for the generation of the weapon signature for snipers using experi-

8. The models can be used in the fast-running forward problem solver (FPS) to calculate the overpressure loading on soldiers from the weapon blast. In addition, this capability is further improved by the implementation of ground-reflection simulators into the tool in addition to the loading due to the blast source. An analytical calculation of blast overpressure from the reflected blast wave from the ground is also included into this improved FPS solver as shown in FIGS. 23A-26. The segmented models enable us to calculate body-region specific overpressure loading, blast metrics and injury criterion as shown in FIG. 26.

The accuracy of the disclosed system and method to estimate the weapon-induced blast loads during a training/combat scenario depends on the knowledge of the positioning and posture of the human body models, and the accuracy of the weapon signature model (e.g., calculated from pressure traces in body-worn sensors and knowledge of position of these sensors with respect to the blast source). To demonstrate the robustness and accuracy of the disclosed system and method, the method can use the published and experimental data from field training scenarios to compare the pressure profile predictions.

Published experimental data of pressure traces from field sensors during the firing of a Carl Gustav recoilless rifle was used to successfully calibrate and compare the model predictions to that of the simulated results. The input training gunner setup is shown in FIG. 27, and the corresponding simulated pressure traces at the virtual pressure sensors, using the disclosed system and method, are compared against experimental data (FIG. 28A-C). A high degree of agreement between "measured" pressure traces from FPS simulations and predicted pressure traces from blast sensors has been achieved.

Experimental data of pressure traces from field sensors during sniper training was used to successfully generate the "Weapon Signature" and validated using the pressure trace data from body-worn pressure sensors. Due to the absence of time-gated data sets, parametric FPS were used to generate the "Weapon Signature" from the field sensor data. Time-shifting was performed on pressure traces from each of the virtual pressure sensors to match the real sensor data. This weapon signature was subsequently used to simulate overpressure exposure and compare the pressure traces at virtual pressure sensors against that of the real pressure sensors (FIG. 29).

In some embodiments, a system and method is provided for automated model-based calculations of blast loads on humans that are exposed to blast waves generated by explosive materials and high-power weapons during military training and combat. The systems are configured to implement the methods. The methods can include generation of weapon or explosive material "weapons signatures" in terms of a "blast wave kernel" with weapon specific physical parameters and properties. The methods can include generation of a physical scene of military training of gunners, snipers, artillery and mortar crews exposed to blast waves generated by explosive materials and high-power weapons. The methods can include calculation of spatially distributed and time-resolved blast loads on human subjects, animals, vehicles, buildings, or other objects exposed to blast waves during military training and combat. The methods can include calculation of blast loads on any part of the human body including blast injury sensitive organs such a head, face, ears, chest/lung and others. The methods can include calculation of blast specific "dose" parameters such as maximum overpressure, impulse, force vector and moments on the organ and others that could be used in medical diagnostics and protective decisions. The methods can calculate and provide a personalized estimate of blast exposure for different soldiers involved in the training scene. Also, methods are provided to validate the model using wearable blast sensor data.

In some embodiments, the methods can be used to generate calculated data sets that can be used in the development of predictive machine learning algorithms that can assist in personalized decision making.

The systems can be configured for sending sensor data to a computer or cloud system and computing and reporting blast strength, location and blast wave loading on targets.

The methods can be used for a human subject or a plurality of human subjects involved in weapons training, such as soldiers and instructors using high power weapons in combat. The individual weapon systems can be experimentally tested to generate the weapon specific blast wave signature ("weapon signature"). The pressure sensors can record pressure as a function of time induced by the blast waves generated by weapons or explosives. The specific weapon signature can be determined by analyzing experimental sensor data using an Inverse Problem Solver (IPS). The calculations can be used to optimize the location of wearable pressure sensors on a human body for accurate collection of specific weapons and training scenes. The pressure traces of non-gated sensors can be analyzed and time-aligned. The explosion blast loading on human bodies and equipment can be determined by using the "weapon signature" or "blast wave kernel" as initial conditions for the FPS simulation. The distributed and integrated blast loads can be calculated on any part of the human body, and a blast "dose" can be determined for blast injury sensitive organs such as head, face, ears, chest/lung and others. The "dose-response" calculations can be used in which the blast "dose" is correlated to a physiological "response," such as cognitive, physiological or biological biomarkers. The blast loading data on specific organs are used to compute organ specific injury criteria. The method and system enabling sensor data collection on mobile platforms, data processing and storage on the web or cloud for future analytics of human body exposure to multiple loads. The results of the calculations can be provided in reports for assessment for future training drills and live military activity, and determining whether or not a soldier should be protected from blasts, removed from potential blast areas, or given improved blast protection equipment as well as for other uses. The reports can also be used to determine whether or not a soldier needs medical care in response to blast loading.

Forward Problem System

The forward problem system solves compressible gas dynamics equations as following. Mass continuity equation:

$$\frac{\partial \rho}{\partial t} + \frac{\partial \rho u_j}{\partial x_j} = 0 \qquad (1)$$

Momentum conservation equation or Navier Stokes equations:

$$\frac{\partial \rho u_i}{\partial t} + \frac{\partial}{\partial x_j}\rho u_j u_i = -\frac{\partial p}{\partial x_i} + \frac{\partial \tau_{i,j}}{\partial x_j} + F_i \qquad (2)$$

Energy Conservation Equation:

$$\frac{\partial \rho H}{\partial t} + \frac{\partial}{\partial x_j}\rho u_j H = \frac{\partial}{\partial x_j} k \frac{\partial T}{\partial x_j} + \frac{\partial}{\partial x_j} u_i \tau_{j,k} \delta_{i,k} + \frac{\partial p}{\partial t} + S_H \qquad (3)$$

Here, $\rho$ is the gas density, $u_j$ is the $j^{th}$ component of velocity vector, p is the static pressure, $\tau$ is the viscous stress tensor, $F_i$ is the body force, H is the total enthalpy, T is the temperature, k is the conductivity, $S_H$ is the additional source. $\delta_{ij}$ is the Kronecker delta and is defined as:

$$\delta_{i,j} = \begin{cases} 1, & i = j \\ 0, & i \neq j \end{cases}$$

The viscous stress tensor $\tau$ is:

$$\tau_{i,j} = \mu\left(\frac{\partial u_i}{\partial x_j} + \frac{\partial u_j}{\partial x_i}\right) - \frac{2}{3}\mu \frac{\partial u_k}{\partial x_k}\delta_{i,j} \qquad (4)$$

Here $\mu$ is the fluid dynamic viscosity. For idea gas, the density is calculated using the idea gas law:

$$p = \rho \frac{R_0}{W} T \quad (5)$$

Here $R_0$ is the universal gas constant and W is the gas molecular weight. Equation (1) through (5) can be integrated and solved via finite volume method over a control volume. An example protocol can use SIMPLE-C algorithm to solve for Equation (1) through (5) [Jiang 1994, Chen 2010].

Optimization Algorithm:
Levenberg-Marquardt Method

One of the optimization methods can include the Levenberg-Marquardt (LM) least square algorithm [Levenberg 1944, Marquardt 1963]. In LM method, the objective function for the optimization can be formulated as:

$$\varepsilon = \frac{1}{2} \sum_{i=1}^{N} [d(t_i) - f(t_i, p)]^2 = \frac{1}{2} \Delta^T \Delta \quad (6)$$

Here, $d(t_i)$, i=1, 2, ... N are experimental measurements at time t, the theoretical model, $f(t_i,p)$ contains a set of linearly independent model coefficients $p\{p_1, p_2, \ldots p_m\}$ the superscript "T" denotes transpose, $\Delta$ is an (N×1) dimensional vector of model and experimental deviation at each time point, and $\varepsilon$ is the total scalar sum of squared error. The goal is to minimize $\varepsilon$ by systematically varying the adjustable model coefficients, p.

The least square error, $\varepsilon$, is minimum when the gradient of $\varepsilon$ with respect to model coefficient p is zero. We denote the $j^{th}$ component of the (M×1) dimensional gradient vector, G, as:

$$G_j = \frac{\partial \varepsilon}{\partial p_j} = \sum_{i=1}^{N} \left(\frac{\partial \Delta_i}{\partial p_j}\right) \Delta_i \quad (7)$$

Where $\partial \varepsilon / \partial p_j$ is gradient Jacobian. We are seeking the set of parameters p* such that two-norm, $\|G(p^*)\|=0$ or more practically $\|G(p^*)\|<\delta$, where $\delta$ is the convergence criteria.

The LM algorithm seeks an iterative solution to the above problem which requires to compute the descent direction s such that $p^{n+1}=p_n+s$ resulting in $\varepsilon(p^{n+1})<\varepsilon(p^n)$. However, LM method highly relies on the gradient Jacobian calculation.

DAKOTA Package

Another optimization software package DAKOTA (A Multilevel Parallel Object-Oriented Framework for Design Optimization, Parameter Estimation, Uncertainty Quantification, and Sensitivity Analysis) [Brain, et. al., 2015] can provide several optimization methods. One of them is modified multi objective minimization method. DAKOTA considers the following minimization problem:

Minimize: $f(x), x \in R^n$ $g_L \leq g(x) \leq g_U$ $h(x) = h_t \quad (8)$

Subject to: $a_L \leq A_i x \leq a_U \quad (9)$ $A_e x = a_t$ $x_L \leq x \leq x_U \quad (8)$ Here $x=(x_1, x_2, \ldots x_n)$ is an (n×1) dimensional vector of real value design variables or design parameters. The n-dimensional vectors, $x_L$ and $x_U$ are the lower and upper bounds, respectively, of the design parameters. These bounds define the allowable values for the elements of x, and the set of all allowable values is termed the design space or the parameter space. A design point or a sample point is a particular set of values within the parameter space.

The optimization goal is to minimize the objective function, f(x) while satisfying the constraints. Constraints can be categorized as either linear or nonlinear and as either inequality or equality. The nonlinear inequality constraints, g(x) are "2-sided" in that they have lower and upper bounds, $g_L$ and $g_U$, respectively. The nonlinear equality constraints h(x), have target values specified by $h_t$. The linear inequality constraints create a linear system $A_i x$, where $A_i$ is the coefficient matrix for the linear system. These constraints are also 2-sided as they have lower and upper bounds, $a_L$ and $a_U$, respectively. The linear equality constraints create a linear system $A_e x$, where $A_e$ is the coefficient matrix for the linear system at the target values. The constraints partition the parameter space into feasible and infeasible regions. A design point is said to be feasible if and only if it satisfies all of the constraints. Correspondingly, a design point is said to be infeasible if it violates one or more of the constraints.

Shooting Method

The Shooting method, or its variant Golden Ratio method, can be used to solve inverse problems for predicting model coefficients [Kiefer 1953, Avriel 1966]. In the IED explosion situation, the model coefficients include explosion charge mass and locations relative to sensor. Since the optimization algorithm in the current paper is based on either minimization or maximization problem, we use FIG. 9 to show the detailed solution procedure. In FIG. 9, $\varepsilon(u)$ denotes the least square error between the simulated and measured physical field quantity, u, such as gas pressure, temperature or chemical species concentration.

The optimization algorithm used for the disclosed method involves the following iterative steps for each of the u parameters: (1) evaluate system least square error $\varepsilon(a)$ between the simulated and measured data at the lower bound, $u_{LB}$, and the upper bound $u_{UB}$; (2) Randomly pick third input parameter $_{u1}$ for obtaining the model error $\varepsilon(u_1)$ between the simulated and measured data; (3) If $\varepsilon(u_1)<\varepsilon$ ($u_{LB}$), then the next guess parameter $u_2$ is located between ($u_1$, $u_{UB}$), otherwise i.e., if $\varepsilon(u_1)>\varepsilon(u_{LB})$, the next guess parameter $u_2$ is selected between ($u_{LB}$, $u_1$); (4) Define non-dimensional parameter $\xi=(u-u_{LB})/(u_{UB}-u_{LB})$, $(0 \leq \xi \leq 1)$, the new parameter is calculated either by mean value $\xi_2=0.5$ ($\xi_1+1$) or golden ratio $\xi_2=0.5(\sqrt{5}-1)(\xi_1+1)=0.618(\xi_1+1)$; and (5) Continue the steps (3) and (4) until finding the desired match between measured and predicted u parameters.

For this and other processes and methods disclosed herein, the operations performed in the processes and methods may be implemented in differing order. Furthermore, the outlined operations are only provided as examples, and some operations may be optional, combined into fewer operations, eliminated, supplemented with further operations, or expanded into additional operations, without detracting from the essence of the disclosed embodiments.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only, and is not intended to be limiting.

In one embodiment, the present methods can include aspects performed on a computing system. As such, the computing system can include a memory device that has the computer-executable instructions for performing the methods. The computer-executable instructions can be part of a computer program product that includes one or more algorithms for performing any of the methods of any of the claims.

In one embodiment, any of the operations, processes, or methods, described herein can be performed or cause to be performed in response to execution of computer-readable instructions stored on a computer-readable medium and executable by one or more processors. The computer-readable instructions can be executed by a processor of a wide range of computing systems from desktop computing systems, portable computing systems, tablet computing systems, hand-held computing systems, as well as network elements, and/or any other computing device. The computer readable medium is not transitory. The computer readable medium is a physical medium having the computer-readable instructions stored therein so as to be physically readable from the physical medium by the computer/processor.

There are various vehicles by which processes and/or systems and/or other technologies described herein can be affected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The various operations described herein can be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware are possible in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a physical signal bearing medium include, but are not limited to, the following: a recordable type medium such as a floppy disk, a hard disk drive (HDD), a compact disc (CD), a digital versatile disc (DVD), a digital tape, a computer memory, or any other physical medium that is not transitory or a transmission. Examples of physical media having computer-readable instructions omit transitory or transmission type media such as a digital and/or an analog communication medium (e.g., a fiber optic cable, a waveguide, a wired communication link, a wireless communication link, etc.).

It is common to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. A typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems, including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. Such depicted architectures are merely exemplary, and that in fact, many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to: physically mateable and/or physically interacting components and/or wirelessly interactable and/or wirelessly interacting components and/or logically interacting and/or logically interactable components.

Figure 17:
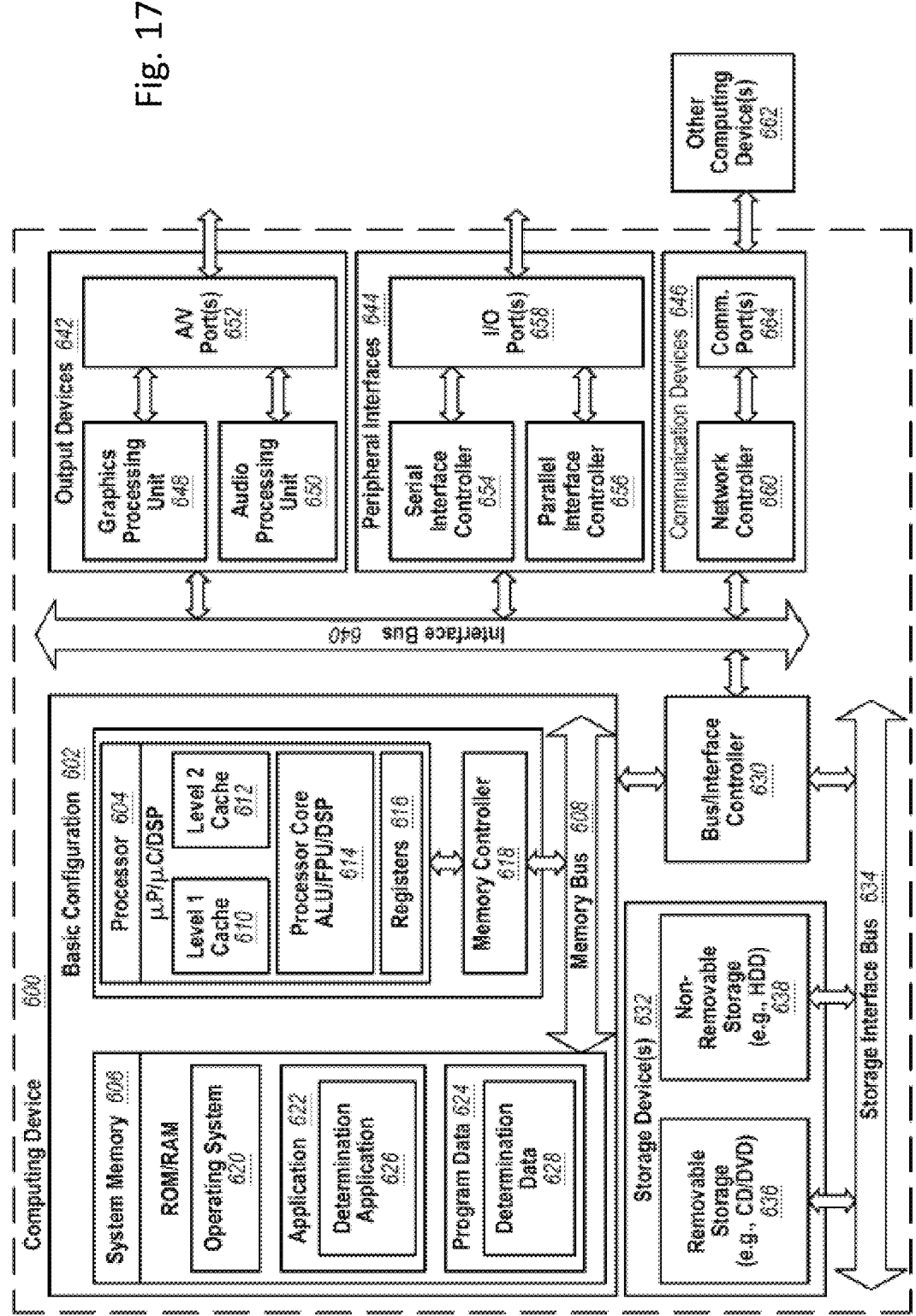
FIG. 17 shows a computing system that can be used to perform the computations of the methods.

FIG. 17 shows an example computing device 600 (e.g., a computer) that may be arranged in some embodiments to perform the methods (or portions thereof) described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including, but not limited to: a microprocessor (µP), a microcontroller (µC), a digital signal processor (DSP), or any combination thereof. Processor 604 may include one or more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations, memory controller 618 may be an internal part of processor 604.

Depending on the desired configuration, system memory 606 may be of any type including, but not limited to: volatile memory (such as RAM), non-volatile memory (such as ROM, flash memory, etc.), or any combination thereof. System memory 606 may include an operating system 620, one or more applications 622, and program data 624. Application 622 may include a determination application 626 that is arranged to perform the operations as described herein, including those described with respect to methods described herein. The determination application 626 can obtain data, such as pressure, flow rate, and/or temperature, and then determine a change to the system to change the pressure, flow rate, and/or temperature.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include: magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include: volatile and non-volatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to: RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

Avriel, M., Wilde, Douglass J. (1966), "Optimality Proof for the Symmetric Fibonacci Search Technique", Fibonacci Quarterly, Vol. 4: 265-269.

Axelsson H, Yelverton J T. (1996) Chest wall velocity as a predictor of nonauditory blast injury in a complex wave environment. J Trauma. 40 (3 Suppl): S31-7.

Carr W, Polejaeva E, Grome A, et al (2015) Relation of Repeated Low-Level Blast Exposure With Symptomology Similar to Concussion," J Head Trauma Rehab. 30(1):47-55.

Carr W, Stone J R, Walilko T, et al (2016) Repeated Low-Level Blast Exposure: A Descriptive Human Subjects Study. Military Medicine, 181, 5:28-39

CONWEP, 1993, US Army Corps of Engineers, Vicksburg, USA.

Gupta R K and Przekwas A. (2013) Mathematical models of blast induced TBI: current status, challenges and prospects, Frontiers in Neurotrauma, 4:59, 2013.

Hutchinson J, Kaiser M J, Lankarani H M, (1998) The Head Injury Criterion (HIC) functional, Applied Mathematics and Computation 96 (1998) 1-16.

Kamimori G H, Reilly L A, LaValle C R, Olaghere Da Silva U B. (2017) Occupational overpressure exposure of breachers and military personnel. Shock Waves, 27 (6); 837-847.

Kiefer, J. (1953), "Sequential Minimax Search for a Maximum", Proceedings of the American Mathematical Society, Vol. 4 (3): 502-506.

Kingery, C. N. and Bulmash, G. (1984): Air-Blast Parameters from TNT Spherical Airburst and Hemispherical Surface Burst. ABRL-TR-0255. U.S. Army Ballistic Research laboratory.

Marjoux D, Baumgartner D, Deck C, Willinger R (2008) Head injury prediction capability of the HIC, HIP, SIMon and ULP criteria. Accident Analysis and Prevention 40; 1135-48

Przekwas A. (2008) Multiscale Modeling of Lung Blast Injuries. Book Chapter in "Explosion and Blast Injuries" Ed. by Nabil Elsayed and James Atkins. Elsevier 2008

Tan X G, Przekwas A, Rule G, Iyer K, Ott K, Merkle A. (2011) Modeling Articulated Human Body Dynamics Under a Representative Blast Loading. ASME Int. Mech. Eng. Congress and Exposition, Vol. 2: Biomedical and Biotechnology Engineering; Nanoengineering for Medicine and Biology, Denver, Colo., Nov. 11-17, 2011

Wiri S, Needham C (2016) Reconstruction of improvised explosive device blast loading to personnel in the open. Shock Waves 26:279-286

Wiri S, Ritter A C, Bailie J M, Needham C, Duckworth J L. (2017) Computational modeling of blast exposure associated with recoilless weapons combat training. Shock Waves, 27 (6) 849-862

Zhou X, Sun K, Roos P E, Li P, Corner B. (2016) Anthropometry model generation based on ANSUR II database. Int. J. Digital Human, 1 (4); 321-343

CROSS-REFERENCE

This patent application cross-references U.S. Provisional Application No. 62/780,806 filed Dec. 17, 2018, which provisional is incorporated herein by specific reference in its entirety.

The invention claimed is:

1. A method of calculating blast injury metrics in a scene, the method comprising:
reconstructing topological layout of the scene having at least one real subject and a blast source;
obtaining and using anthropometric and posture data for each real subject;
obtaining and using anatomical soldier model for each real subject;
identifying real position of at least one real pressure sensor on each soldier during a blast;
positioning a virtual sensor on each anatomical soldier model to correspond with real pressure sensor on the real subject;
calculating weapon signature of the blast source using body-worn and free-field ambient pressure sensor data, the weapon signature including pressure versus time for a blast from the blast source;
generating simulated pressure traces on each anatomical soldier model at each virtual pressure sensor;
calculating blast injury metrics for the at least one real subject; and
generating a report that includes the blast injury metrics for the at least one real subject.

2. The method of claim 1, wherein the blast injury metrics include at least one of peak overpressure, peak force, positive impulse, negative impulse, organ specific injury criteria, and injury diagnosis.

3. The method of claim 1, wherein the scene includes position and orientation of the at least one real subject and blast source relative to each other.

4. The method of claim 3, further comprising identifying a relative position for each real subject with respect to each other by using the blast source position and orientation as a reference.

5. The method of claim 4, further comprising generating the anatomical soldier model for each real subject.

6. The method of claim 5, wherein the anatomical soldier model includes a three-dimensional skin model equipped with clothing and protective armor articulated into a pose.

7. The method of claim 6, wherein each virtual pressure sensor is placed corresponding to its position relative to the blast source in the real scene.

8. The method of claim 7, further comprising generating the weapon signature or obtaining a pre-determined weapon signature for the blast source.

9. The method of claim 1, further comprising evaluating the accuracy of the blast injury metrics by comparing pressure data of the at least one real pressure sensor with each corresponding virtual pressure sensor.

10. The method of claim 1, further comprising generating an anatomical soldier model by:
obtaining a three dimensional skin model;
equipping the three dimensional skin model with virtual clothing and virtual protective armor to obtain a virtual soldier model;
segmenting the virtual soldier model into different anatomical body regions;
articulating segmented virtual soldier model into a pose of a real subject of a blast scene;
generating a surface mesh of the articulated segmented virtual soldier model; and
generating a report that includes the articulated segmented virtual soldier model and the real subject of the blast.

11. The method of claim 10, further comprising:
generating an integrated geometry model from the virtual soldier model;
obtaining data for anatomically consistent joint locations on the virtual soldier model;
creating joint planes at the joint locations;
generating intersection loops at the joint locations in order to smooth an intersection between different anatomical regions on the virtual soldier model;
generating bounding boxes with faces including the joint planes;
segmenting the virtual soldier model into the different anatomical regions based on locations of triangular patches of a surface of the virtual soldier model with respect to the bounding boxes; and
articulating the segmented virtual soldier model into a pose of a real subject of a blast scene.

12. The method of claim 1, further comprising calculating a weapon signature for a blast source of a weapon by:
obtaining pressure data from a plurality of pressure sensors that recorded pressure during a scene;
obtaining topological layout of the plurality of pressure sensors with respect to the blast source;
reconstructing scene to place a virtual pressure sensor at a position for each of the plurality of pressure sensors;
obtaining time-gated pressure trace data for each of the plurality of pressure sensors;
processing the time-gated pressure trace data to obtain a blast wave at the blast source;
defining the blast wave at the blast source as a weapon signature for the weapon; and
generating a report to include the weapon signature for the weapon.

13. A method of generating an anatomical soldier model, the method comprising:
obtaining a three-dimensional skin model;
equipping the three-dimensional skin model with virtual clothing and virtual protective armor to obtain a virtual soldier model;
segmenting the virtual soldier model into different anatomical body regions;
articulating segmented virtual soldier model into a pose of a real subject of a blast scene;
generating a surface mesh of the articulated segmented virtual soldier model; and
generating a report that includes the articulated segmented virtual soldier model and the real subject of the blast.

14. The method of claim 13, further comprising:
obtaining body scan data of the real subject; and
generating the three dimensional skin model.

15. The method of claim 13, further comprising:
obtaining anthropometric data for the real subject; and
generating the three dimensional skin model using a body model generator.

16. The method of claim 13, further comprising calculating blast injury metrics for the at least one real subject with the articulated segmented virtual soldier model.

17. The method of claim 13, further comprising:
generating an integrated geometry model from the virtual soldier model;
obtaining data for anatomically consistent joint locations on the virtual soldier model;
creating joint planes at the joint locations;
generating intersection loops at the joint locations in order to smooth an intersection between different anatomical regions on the virtual soldier model;
generating bounding boxes with faces including the joint planes;
segmenting the virtual soldier model into the different anatomical regions based on locations of triangular patches of a surface of the virtual soldier model with respect to the bounding boxes; and
articulating the segmented virtual soldier model into a pose of a real subject of a blast scene.

18. A method of calculating a weapon signature for a blast source of a weapon, the method comprising:
obtaining pressure data from a plurality of pressure sensors that recorded pressure during a scene;
obtaining topological layout of the plurality of pressure sensors with respect to the blast source;
reconstructing scene to place a virtual pressure sensor at a position for each of the plurality of pressure sensors;
obtaining time-gated pressure trace data for each of the plurality of pressure sensors;
processing the time-gated pressure trace data to obtain a blast wave at the blast source;
defining the blast wave at the blast source as a weapon signature for the weapon; and
generating a report to include the weapon signature for the weapon.

19. The method of claim 18, further comprising:
obtaining pressure data that is not time-gated; and
converting the pressure data to time gated pressure data.

20. The method of claim 19, further comprising:
generating virtual pressure traces from the pressure data that is not time-gated;
perform a time shift on the virtual pressure traces to match arrival time of the pressure data that is not time-gated;
determine an error between the virtual pressure traces and the pressure data; and
determine whether or not the error is acceptable;
if acceptable, use the virtual pressure traces; or
if not acceptable, modify blast wave kernel data and generate new virtual pressure traces for time shifting and error determination.

* * * * *